(12) United States Patent
Sutton et al.

(10) Patent No.: US 12,171,784 B2
(45) Date of Patent: Dec. 24, 2024

(54) PLATELET LYSATE COMPOSITIONS AND USES THEREOF

(71) Applicant: iFix Medical Pty Ltd, Sydney (AU)

(72) Inventors: Gerard Sutton, Balmoral (AU); JingJing You, Ryde (AU); Hannah Frazer, East Killara (AU)

(73) Assignee: iFix Medical Pty Ltd, Sydney (AU)

( * ) Notice: Subject to any disclaimer, the term of this patent is extended or adjusted under 35 U.S.C. 154(b) by 882 days.

(21) Appl. No.: 17/265,936

(22) PCT Filed: Aug. 7, 2019

(86) PCT No.: PCT/AU2019/050822
§ 371 (c)(1),
(2) Date: Feb. 4, 2021

(87) PCT Pub. No.: WO2020/028944
PCT Pub. Date: Feb. 13, 2020

(65) Prior Publication Data
US 2021/0290683 A1    Sep. 23, 2021

(30) Foreign Application Priority Data
Aug. 7, 2018   (AU) ............................... 2018902870

(51) Int. Cl.
| | | |
|---|---|---|
| *A61K 35/19* | (2015.01) |
| *A61J 1/20* | (2006.01) |
| *A61K 31/43* | (2006.01) |
| *A61K 31/7048* | (2006.01) |
| *A61K 33/06* | (2006.01) |
| *A61K 33/14* | (2006.01) |
| *A61K 38/18* | (2006.01) |
| *A61K 38/36* | (2006.01) |
| *A61K 38/39* | (2006.01) |
| *A61K 38/45* | (2006.01) |
| *A61K 38/48* | (2006.01) |
| *A61K 45/06* | (2006.01) |
| *A61L 26/00* | (2006.01) |
| *A61L 27/22* | (2006.01) |
| *A61L 27/36* | (2006.01) |
| *A61P 17/02* | (2006.01) |
| *A61P 27/02* | (2006.01) |
| *B29C 64/106* | (2017.01) |
| *B33Y 40/10* | (2020.01) |
| *B33Y 70/00* | (2020.01) |

(52) U.S. Cl.
CPC ............ *A61K 35/19* (2013.01); *A61J 1/2093* (2013.01); *A61K 31/43* (2013.01); *A61K 31/7048* (2013.01); *A61K 33/06* (2013.01); *A61K 33/14* (2013.01); *A61K 38/1808* (2013.01); *A61K 38/363* (2013.01); *A61K 38/39* (2013.01); *A61K 38/45* (2013.01); *A61K 38/4833* (2013.01); *A61K 45/06* (2013.01); *A61L 26/0042* (2013.01); *A61L 26/0047* (2013.01); *A61L 26/0057* (2013.01); *A61L 27/225* (2013.01); *A61L 27/227* (2013.01); *A61L 27/3616* (2013.01); *A61P 17/02* (2018.01); *A61P 27/02* (2018.01); *B29C 64/106* (2017.08); *B33Y 40/10* (2020.01); *B33Y 70/00* (2014.12); *A61K 38/18* (2013.01); *A61K 2300/00* (2013.01); *A61L 2430/16* (2013.01)

(58) Field of Classification Search
CPC ... A61J 1/2093; A61K 31/43; A61K 31/7048; A61K 33/06; A61K 33/14; A61K 35/19; A61K 38/18; A61K 38/1808; A61K 38/363; A61K 38/39; A61K 38/45; A61K 38/4833; A61K 45/06; A61K 2121/00; A61K 2300/00; A61L 26/009; A61L 26/0042; A61L 26/0047; A61L 26/0057; A61L 27/225; A61L 27/227; A61L 27/3616; A61L 27/58; A61L 2430/16; A61P 17/02; A61P 27/02; B29C 64/106; B33Y 40/10; B33Y 70/00; B33Y 10/00
See application file for complete search history.

(56) References Cited

U.S. PATENT DOCUMENTS

| | | |
|---|---|---|
| 7,196,054 B1 | 3/2007 | Drohan et al. |
| 2011/0213319 A1 | 9/2011 | Blott et al. |
| 2017/0252411 A1 | 9/2017 | Brewster et al. |

FOREIGN PATENT DOCUMENTS

| | | |
|---|---|---|
| JP | 2014-533715 | 12/2014 |
| WO | 2011/110948 | 9/2011 |
| WO | 2013/076507 | 5/2013 |
| WO | WO 2020/028944 | 2/2020 |

OTHER PUBLICATIONS

International Search Report for PCT/AU2019/050822. Mailed Sep. 25, 2019. 4 pages.
Ahmed et al., Fibrin: a versatile scaffold for tissue engineering applications. Tissue Eng Part B Rev. Jun. 2008;14(2):199-215.

(Continued)

*Primary Examiner* — John Kim
(74) *Attorney, Agent, or Firm* — Casimir Jones, S.C.; Robert A. Goetz

(57) ABSTRACT

The present invention relates to compositions, kits, and methods for providing mechanical support and/or agents to biological targets. Specifically, the compositions comprise platelet lysate, fibrinogen and thrombin. The compositions can be used for the treatment of wounds/injuries (e.g. corneal), and for other applications including tissue culture.

5 Claims, 22 Drawing Sheets

(56) References Cited

OTHER PUBLICATIONS

Burnouf et al., Human platelet lysate: Replacing fetal bovine serum as a gold standard for human cell propagation? Biomaterials. Jan. 2016;76:371-87.

Burnouf, Current methods to manufacture human platelet lysates and possible trends in product safety and standardisation. Vox Sanguinis, 2016, vol. 111, supl 1 pp. 39. abstract 3D-S11-02.

Chou et al., Current methods to manufacture human platelet lysates for cell therapy and tissue engineering: possible trends in product safety and standardization. ISBT Science Series, 2017, vol. 12, Issue 1, pp. 168-175.

Faramarzi et al., Patient-Specific Bioinks for 3D Bioprinting of Tissue Engineering Scaffolds. Adv Healthc Mater. Jun. 2018;7(11):e1701347. 1-17.

Kinzebach et al., Functional and differential proteomic analyses to identify platelet derived factors affecting ex vivo expansion of mesenchymal stromal cells. BMC Cell Biol. Oct. 30, 2013;14:48. 1-13.

Rajabzadeh et al., Morphological study of isolated ovarian preantral follicles using fibrin gel plus platelet lysate after subcutaneous transplantation. Cell J. 2015 Spring;17(1):145-52.

Wanner et al., Platelet Lysate: The Better Choice for Jaw Periosteal Cell Mineralization. Stem Cells Int. 2017;2017:8303959. 1-10.

Copland et al.The effect of platelet lysate fibrinogen on the functionality of MSCs in immunotherapy, Biomaterials 34 (2013) 7840-7850.

A

B

PLATELET LYSATE COMPOSITIONS AND USES THEREOF

INCORPORATION BY CROSS-REFERENCE

The present application claims priority from Australian provisional application number 2018902870 filed on 7 Aug. 2018, the entire contents of which are incorporated herein by cross reference.

TECHNICAL FIELD

The present invention relates generally to the fields of biology and medicine, and more specifically to compositions and methods for providing mechanical support and/or agents to biological targets. Still more specifically the present invention relates to compositions and methods which can be used for the treatment of wounds/injuries, and for other applications including tissue culture.

BACKGROUND

The cornea is an integral component of the anterior ocular surface that refracts light through the pupil and serves as a physical barrier to infection, UV light and mechanical trauma. Further, corneal injuries represent the most common ophthalmic emergency presentation in Australia and approximately 75% of all cases are due to the presence of foreign bodies or abrasions in the cornea. These injuries alone are estimated to cost the Australian population more than $155 million per year and if not treated effectively, can lead to infection and scarring resulting in permanent, impaired vision. In addition, corneal disease is the second most common cause of blindness in most developing countries with an estimated 12% of the 39 million blind people worldwide suffering from bilateral corneal blindness and an additional 23 million people suffering from unilateral corneal blindness.

Corneal defects can arise from trauma and other disease processes. In mild cases, the cornea is able to regenerate via normal wound healing pathways and due to the dense neuronal innervation of the cornea, corneal injuries can be extremely painful. In some cases however, the cornea's normal wound healing mechanism may be insufficient. This leads to the formation of non-healing defects which can result in corneal melting, corneal neovascularisation, loss of transparency, infection, scarring and diminished vision to the point of blindness.

Corneal wound healing occurs when the equilibrium between cell replenishment and cell loss is disrupted such as after an abrasion, infection or refractive surgery. In mild cases, the cornea can upregulate physiological processes to restore this disequilibrium, however, in more severe cases, additional treatment is required. In cases where wound healing does not effectively occur, potentially detrimental outcomes such as impaired vision and even corneal blindness can result.

Current medical treatments for corneal injuries include antibiotics, eye pads, sutures and surgical glues, which may help in minor wounds. However, they do not adequately address issues arising in more advanced wounds including pain relief, infection and/or the development of scar tissue. Infection represents a significant complication and may require hospitalisation. These issues are not restricted only to corneal injuries, and prevail in the case of wounds in other body tissues as well. Scarring, common in severe corneal injuries, can lead to permanent vision loss with corneal transplantation the only option for visual rehabilitation.

A need exists for improved compositions and methods for treating corneal injuries. The improved compositions and methods may also find application in the treatment of wounds in other tissues.

SUMMARY OF THE INVENTION

The present invention alleviates at least one of the problems associated with current compositions and/or methods for treating wounds (e.g. corneal wounds).

The mechanical properties of platelet lysate are similar to those of water thus making it difficult to apply to tissue in a structured form. For example, it is very challenging and in most cases unfeasible to apply raw platelet lysate layer-by-layer to a tissue in order to generate two- or three-dimensional structures (e.g. as necessary for techniques such as bioprinting). The present inventors have developed platelet lysate compositions with mechanical and structural properties that facilitate application to tissue in a structured form. In particular, the compositions of the present invention may be used to apply platelet lysates to tissue (e.g. eye) using two- or three-dimensional bioprinting techniques. The compositions may be prepared from initially separated components collectively comprising at least platelet lysate, fibrinogen, and thrombin. When mixed the separated components solidify into a gel-like material comprising the platelet lysate. The rate of solidification may be controlled by varying the timing and/or amount of various composition component/s, thus providing flexibility in the application process. Without limitation, the compositions and methods described herein are generally useful for the delivery of agents (e.g. drugs and/or or other substances) to biological targets (e.g. tissue, membranes, cells) find application, for example, in the treatment of wounds, including wounds in corneal tissue (e.g. non-healing corneal ulcers or abrasions)

The present invention relates at least in part to the following embodiments:

Embodiment 1. A composition comprising 0.1-20 mg/ml fibrinogen, 2-20 U/mL thrombin, and 1-40% (v/v) platelet lysate.

Embodiment 2. The composition of embodiment 1, further comprising any one or more of: ions, an ion source, amino acids, fibronectin, anaesthetics, antibiotics, growth factors, tissue factor XIII, matrix proteins (e.g. collagen).

Embodiment 3. The composition of embodiment 1 or embodiment 2, wherein the ions comprise calcium ions, and/or the growth factors comprise human epidermal growth factor (hEGF).

Embodiment 4. The composition of any one of embodiments 1 to 3, wherein the composition comprises a culture medium comprising the ions and amino acids.

Embodiment 5. The composition of any one of embodiments 1 to 4, wherein the ions are components of an ionic salt solution included in the composition.

Embodiment 6. The composition of any one of embodiments 1 to 5, wherein the composition further comprises cells (e.g. mammalian cells, human cells).

Embodiment 7. The composition of any one of embodiments 1 to 6, wherein the platelet lysate comprises or consists of human platelet lysate.

Embodiment 8. The composition of any one of embodiments 1 to 7, wherein the platelet lysate is free or substantially free of anticoagulants (e.g. heparin), or comprises less than: 10% (v/v), 9% (v/v), 8% (v/v), 7% (v/v), 6% (v/v), 5% (v/v), 4% (v/v), 3% (v/v), 2% (v/v), 1% (v/v), 0.5% (v/v), anticoagulants (e.g. heparin).

Embodiment 9. The composition of any one of embodiments 1 to 8, wherein the composition comprises:
   (i) 0.1-15 mg/ml fibrinogen; 2-15 U/ml thrombin; and 5-40% (v/v) platelet lysate; or
   (ii) 0.1-10 mg/ml fibrinogen; 2-10 U/ml thrombin; and 10-35% (v/v) platelet lysate; or
   (iii) 0.2-5 mg/ml fibrinogen; 2-8 U/ml thrombin; and 15-30% (v/v) platelet lysate; or
   (iv) 0.2-3 mg/ml fibrinogen; 2-4 U/ml thrombin; and 15-25% (v/v) platelet lysate.

Embodiment 10. The composition of any one of embodiments 1 to 8, wherein the composition comprises:
   (i) less than 1 mg/ml (e.g. about 0.2 mg/ml) fibrinogen; 2-20 U/ml (e.g. about 3 U/ml, about 5 U/ml, about 10 U/ml) thrombin; and 5-40% (v/v) (e.g. about 20-30% (v/v)) platelet lysate; or
   (ii) 1-4 mg/ml (e.g. about 2 mg/ml) fibrinogen; 5-15 U/ml (e.g. about 7 U/ml, about 10 U/ml, about 12 U/ml) thrombin; and 10-40% (v/v) (e.g. about 15-30% (v/v)) platelet lysate; or
   (iii) 3-8 mg/ml (e.g. about 5 mg/ml) fibrinogen; 2-15 U/ml (e.g. about 4 U/ml, about 8 U/ml, about 12 U/ml) thrombin; and 15-30% (v/v) (e.g. about 20-25% (v/v)) platelet lysate.

Embodiment 11. The composition of any one of embodiments 1 to 8, wherein the composition comprises:
   (i) about 0.4 mg/ml, about 0.8 mg/ml or about 1 mg/ml fibrinogen, and
      about 2 U/ml, about 10 U/ml or about 20 U/ml thrombin, and
      about 20% (v/v), about 25% (v/v) or about 30% (v/v) platelet lysate; or
   (ii) about 2 mg/ml, about 4 mg/ml, or about 8 mg/ml fibrinogen, and
      about 2 U/ml, about 10 U/ml or about 20 U/ml thrombin, and
      about 10%, about 15% (v/v), or about 20% (v/v) platelet lysate; or
   (iii) about 5 mg/ml, about 10 mg/ml, or about 15 mg/ml fibrinogen, and
      about 2 U/ml, about 10 U/ml or about 20 U/ml thrombin, and
      about 5% (v/v), about 15% (v/v), or about 25% (v/v) platelet lysate.

Embodiment 12. The composition of any one of embodiments 1 to 8, wherein the composition comprises:
   (i) at least: about 0.4 mg/ml fibrinogen, about 2 unit/mL thrombin, and about 20% (v/v) platelet lysate; or
   (ii) at least: about 20% (v/v) platelet lysate, about 4 mg/mL fibrinogen, and about 10 U/mL thrombin.

Embodiment 13. A kit, package or device comprising:
   a first compartment comprising fibrinogen and a second compartment comprising thrombin, wherein the kit, package or device is configured to allow separation of the fibrinogen of the first compartment and the thrombin of the second compartment during and following loading of the fibrinogen and thrombin into the kit, package or device;
   platelet lysate;
   means to facilitate mixing of the fibrinogen of the first compartment with the thrombin of the second compartment, and the platelet lysate.

Embodiment 14. The kit, package or device of embodiment 13, wherein the platelet lysate is located in a third compartment of the kit, package or device, which is configured to allow separation of the platelet lysate of the third compartment from the fibrinogen of the first compartment and the thrombin of the second compartment during and following loading of the fibrinogen, thrombin and platelet lysate into the kit, package or device.

Embodiment 15. The kit, package or device of embodiment 13, wherein the first compartment comprises the fibrinogen and the platelet lysate, and the second compartment comprises the thrombin.

Embodiment 16. The kit, package or device of any one of embodiments 13 to 15, wherein:
   any said compartment further comprises any one or more of: ions, an ion source, amino acids, fibronectin, anaesthetics, antibiotics, growth factors (e.g. hEGF), tissue factor XIII, matrix proteins (e.g. collagen); or
   the kit, package or device comprises a further compartment comprising any one or more of: ions, an ion source, amino acids, fibronectin, anaesthetics, antibiotics, growth factors (e.g. hEGF), tissue factor XIII, matrix proteins (e.g. collagen); wherein the kit, package or device is configured to allow separation of contents of the further compartment from contents of other compartments during and following loading of the kit, package or device.

Embodiment 17. The kit, package or device of embodiment 16, wherein:
   the ions are calcium ions, or
   the ion source is an ionic salt and/or comprises calcium ions.

Embodiment 18. The kit, package or device of any one of embodiments 13 to 17, wherein the means is configured to facilitate mixing of the fibrinogen, thrombin and platelet lysate externally to the kit, package or device.

Embodiment 19. The kit, package or device of any one of embodiments 13 to 18, wherein:
   the means is configured to direct a flow stream of the fibrinogen and a separate flow stream of the thrombin to a point of convergence and thereby facilitate said mixing, and
   at least one of said flow streams comprises the platelet lysate.

Embodiment 20. The kit, package or device of any one of embodiments 13 to 19, wherein either or both of the first and second compartments, and/or a third compartment comprises cells (e.g. mammalian cells, human cells).

Embodiment 21. The kit, package or device of any one of embodiments 13 to 20, wherein the platelet lysate comprises or consists of human platelet lysate.

Embodiment 22. The kit, package or device of any one of embodiments 13 to 21, wherein the platelet lysate is free or substantially free of anticoagulants (e.g. heparin), or comprises less than: 10% (v/v), 9% (v/v), 8% (v/v), 7% (v/v), 6% (v/v), 5% (v/v), 4% (v/v), 3% (v/v), 2% (v/v), 1% (v/v), 0.5% (v/v), anticoagulants (e.g. heparin).

Embodiment 23. The kit, package or device of any one of embodiments 13 to 22, wherein:
   (i) the first compartment comprises 0.1-20 mg/ml fibrinogen; the second compartment comprises 1-40 U/ml thrombin; and the device comprises a total of 5-40% (v/v) platelet lysate; or
   (ii) the first compartment comprises 0.1-15 mg/ml fibrinogen; the second compartment comprises 1-30 U/ml thrombin; and the device comprises a total of 5-40% (v/v) platelet lysate; or
   (iii) the first compartment comprises 0.1-12 mg/ml fibrinogen; the second compartment comprises 1-25

U/ml thrombin; and the device comprises a total of 7-14% (v/v) platelet lysate; or (iv) the first compartment comprises 0.5-10 mg/ml fibrinogen; the second compartment comprises 1-10 U/ml thrombin; and the device comprises a total of 0.5-20% (v/v) platelet lysate.

Embodiment 24. The kit, package or device of any one of embodiments 13 to 22, wherein:

(i) the first compartment comprises less than 2 mg/ml (e.g. about 0.8 mg/ml) fibrinogen; the second compartment comprises 0.5-20 U/ml (e.g. about 1 U/ml, about 10 U/ml, about 20 U/ml) thrombin; and the device comprises a total of 5-40% (v/v) (e.g. about 20% (v/v)) platelet lysate; or (ii) the first compartment comprises 1-16 mg/ml (e.g. about 8 mg/ml) fibrinogen; the second compartment comprises 0.5-20 U/ml (e.g. about 1 U/ml, about 10 U/ml, about 20 U/ml) thrombin; and the device comprises a total of 5-40% (v/v) (e.g. about 20% (v/v)) platelet lysate; or (iii) the first compartment comprises 5-15 mg/ml (e.g. about 10 mg/ml); the second compartment comprises 0.5-20 U/ml (e.g. about 1 U/ml, about 10 U/ml, about 20 U/ml) thrombin; and the device comprises a total of 5-40% (v/v) (e.g. about 20% (v/v)) platelet lysate.

Embodiment 25. The kit, package or device of any one of embodiments 13 to 22, wherein:

(i) the first compartment comprises 0.8 mg/ml fibrinogen, and the second compartment comprises about 2 U/ml, about 10 U/ml or about 20 U/ml thrombin, and the device comprises a total of about 20% (v/v) platelet lysate; or (ii) the first compartment comprises about 8 mg/ml fibrinogen, and the second compartment comprises about 2 U/ml, about 10 U/ml or about 20 U/ml thrombin, and the device comprises a total of about 20% (v/v) platelet lysate; or (iii) the first compartment comprises about 20 mg/ml fibrinogen, and the second compartment comprises about 2 U/ml, about 10 U/ml or about 20 U/ml thrombin, and the device comprises a total of about 10% (v/v) platelet lysate.

Embodiment 26. The kit, package or device of any one of embodiments 13 to 22, wherein a formulation arising from the mixing of the thrombin, fibrinogen and platelet lysate comprises:

(i) at least 0.2 mg/ml fibrinogen, at least 1 unit/mL thrombin, and about 10% (v/v) platelet lysate; or (ii) about 20% (v/v) platelet lysate, about 2 mg/mL fibrinogen, and about 5 U/mL thrombin.

Embodiment 27. The kit, package or device of any one of embodiments 13 to 26, wherein the first compartment and the second compartment do not comprise the platelet lysate.

Embodiment 28. The kit, package or device of any one of embodiments 13 to 27, wherein the first compartment and the second compartment are liquid formulations of equal volume, or less than: 1%, 2%, 3%, 4%, 5%, 10%, 15%, 20%, 25%, different in volume.

Embodiment 29. A method of preparing a composition, the method comprising:

(i) providing:
a first formulation comprising fibrinogen and a second formulation comprising thrombin, wherein the first formulation is not in contact with the second formulation; and (ii) mixing the first and second formulations together with platelet lysate to thereby provide the composition.

Embodiment 30. The method of embodiment 29, wherein prior to said mixing the platelet lysate is combined with the first formulation comprising fibrinogen and not combined with the second formulation comprising thrombin.

Embodiment 31. The method of embodiment 29, wherein prior to said mixing the platelet lysate is not combined with the second formulation comprising thrombin.

Embodiment 32. The method of embodiment 29, wherein prior to said mixing the platelet lysate is not combined with the first formulation comprising fibrinogen or the second formulation comprising thrombin.

Embodiment 33. The method of any one of embodiment 29 to 32, wherein the method further comprises mixing any one or more of: ions, an ion source, amino acids, fibronectin, anaesthetics, antibiotics, growth factors (e.g. hEGF), tissue factor XIII, matrix proteins (e.g. collagen); with said first and second formulations and platelet lysate.

Embodiment 34. The method of any one of embodiments 29 to 33, wherein:

the ions are calcium ions, or the ion source is an ionic salt and/or comprises calcium ions.

Embodiment 35. The method of any one of embodiments 29 to 34, further comprising mixing cells (e.g. mammalian cells, human cells) with said first and second formulations.

Embodiment 36. The method of any one of embodiments 29 to 35, wherein the platelet lysate comprises or consists of human platelet lysate.

Embodiment 37. The method of any one of embodiments 29 to 36, wherein the platelet lysate is free or substantially free of anticoagulants (e.g. heparin), or comprises less than: 10% (v/v), 9% (v/v) 8% (v/v), 7% (v/v), 6% (v/v), 5% (v/v), 4% (v/v), 3% (v/v), 2% (v/v), 1% (v/v), 0.5% (v/v), anticoagulants (e.g. heparin).

Embodiment 38. The method of any one of embodiments 29 to 37, wherein:

(i) the first formulation comprises 0.1-20 mg/ml fibrinogen; the second formulation comprises 1-40 U/ml thrombin; and the first and/or second formulations comprise a total of 5-40% (v/v) platelet lysate; or (ii) the first formulation comprises 0.1-15 mg/ml fibrinogen; the second formulation comprises 1-30 U/ml thrombin; and the first and/or second formulations comprise a total of 5-20% (v/v) platelet lysate; or (iii) the first formulation comprises 0.1-12 mg/ml fibrinogen; the second formulation comprises 1-25 U/ml thrombin; and the first and/or second formulations comprise a total of 7-14% (v/v) platelet lysate; or (iv) the first formulation comprises 0.2-10 mg/ml fibrinogen; the second formulation comprises 2-20 U/ml thrombin; and the first and/or second formulations comprise a total of 8-12% (v/v) platelet lysate.

Embodiment 39. The method of any one of embodiments 29 to 37, wherein:

(i) the first formulation comprises less than 1 mg/ml (e.g. about 0.4 mg/ml) fibrinogen; the second formulation comprises 0.5-20 U/ml (e.g. about 1 U/ml, about 10 U/ml, about 20 U/ml) thrombin; and the first and/or second formulations comprise a total of 5-40% (v/v) (e.g. about 20% (v/v)) platelet lysate; or (ii) the first formulation comprises 1-8 mg/ml (e.g. about 4 mg/ml) fibrinogen; the second formulation comprises 0.5-20 U/ml (e.g. about 1 U/ml, about 10 U/ml, about 20 U/ml) thrombin; and the first and/or second formulations comprise a total of 5-40% (v/v) (e.g. about 20% (v/v)) platelet lysate; or (iii) the first formulation comprises 5-15 mg/ml (e.g. about 10 mg/ml); the second formulation comprises 0.5-20 U/ml (e.g. about 1 U/ml, about 10 U/ml, about 20 U/ml) thrombin; and the first and/or second formulations comprise a total of 5-40% (v/v) (e.g. about 20% (v/v)) platelet lysate.

Embodiment 40. The method of any one of embodiments 29 to 37, wherein:

(i) the first formulation comprises about 0.4 mg/ml fibrinogen, and
the second formulation comprises about 2 U/ml, about 10 U/ml or about 20 U/ml thrombin, and
the first and/or second formulations comprise a total of about 10% (v/v) platelet lysate; or (ii) the first formulation comprises about 4 mg/ml fibrinogen, and
the second formulation comprises about 2 U/ml, about 10 U/ml or about 20 U/ml thrombin, and
the first and/or second formulations comprise a total of about 20% (v/v) platelet lysate; or (iii) the first formulation comprises about 10 mg/ml fibrinogen, and
the second formulation comprises about 2 U/ml, about 10 U/ml or about 20 U/ml thrombin, and
the first and/or second formulations comprise a total of about 10% (v/v) platelet lysate.

Embodiment 41. The method of any one of embodiments 29 to 37, wherein the composition comprises:

(i) at least 0.2 mg/ml fibrinogen, at least 1 unit/mL thrombin, and about 20% (v/v) platelet lysate; or (ii) about 20% (v/v) platelet lysate, about 2 mg/mL fibrinogen, and about 5 U/mL thrombin.

Embodiment 42. The method of any one of embodiments 29 to 41, wherein the first formulation and the second formulation are of equal volume, or less than: 1%, 2%, 3%, 4%, 5%, 10%, 15%, 20%, 25%, different in volume.

Embodiment 43. The method of any one of embodiments 29 to 42, wherein the mixing of the first and second formulations and the platelet lysate together comprises:

generating a first flow stream comprising the fibrinogen, a second flow stream comprising the thrombin, and optionally a third flow stream, wherein said flow streams are initially separated from one another, and combining the flow streams together;
and wherein any one or more of the first flow stream, the second flow stream and/or the third flow stream comprises the platelet lysate.

Embodiment 44. A composition obtained by or obtainable by the method of any one of embodiments 29 to 43.

Embodiment 45. Use of the kit, package or device of any one of embodiments 13 to 28 to apply a formulation comprising fibrinogen, thrombin and platelet lysate to tissue of a subject.

Embodiment 46. A method or treating tissue of a subject, the method comprising applying the composition of any one of embodiments 1 to 12 or embodiment 44 to the tissue.

Embodiment 47. A composition of any one of embodiments 1 to 12 or embodiment 44 for use in treating tissue of a subject.

Embodiment 48. Use of a first formulation comprising fibrinogen, and a second formulation comprising thrombin, in the preparation of a medicament for treating tissue of a subject, wherein the medicament further comprises platelet lysate.

Embodiment 49. The use of embodiment 48, wherein the medicament further comprises any one or more of: ions, an ion source, amino acids, fibronectin, anaesthetics, antibiotics, growth factors (e.g. hEGF), tissue factor XIII, matrix proteins (e.g. collagen).

Embodiment 50. The use of embodiment 48 or embodiment 49, wherein the medicament further comprises cells (e.g. mammalian cells, human cells).

Embodiment 51. A first formulation comprising fibrinogen, a second formulation comprising thrombin, and optionally a third formulation, for concurrent use in treating tissue of a subject, wherein any one or more of the first formulation, the second formulation and/or the optional third formulation comprises platelet lysate.

Embodiment 52. The formulations of embodiment 51, wherein:

any one or more of the first formulation, the second formulation and/or the optional third formulation comprises any one or more of: ions, an ion source, amino acids, fibronectin, anaesthetics, antibiotics, growth factors (e.g. hEGF), tissue factor XIII, matrix proteins (e.g. collagen).

Embodiment 53. The formulations of embodiment 51 or embodiment 52, wherein:

any one or more of the first formulation, the second formulation and/or the optional third formulation comprises cells (e.g. mammalian cells, human cells).

Embodiment 54. The use of embodiment 49 or embodiment 50, or the formulations of embodiment 52 to 53, wherein:

the ions are calcium ions, or
the ion source is an ionic salt and/or comprises calcium ions.

Embodiment 55. The use of any one of embodiments 48 to 50 or embodiment 54, or the formulations of any one of embodiments 51 to 54, wherein:

the platelet lysate comprises or consists of human platelet lysate.

Embodiment 56. The use of any one of embodiments 48 to 50, 54 or 55, or the formulations of any one of embodiments 51 to 55, wherein:

the platelet lysate is free or substantially free of anticoagulants (e.g. heparin), or comprises less than: 10% (v/v), 9% (v/v), 8% (v/v), 7% (v/v), 6% (v/v), 5% (v/v), 4% (v/v). 3% (v/v), 2% (v/v), 1% (v/v), 0.5% (v/v), anticoagulants (e.g. heparin).

Embodiment 57. The use of any one of embodiments 48 to 50, or 54 to 56, or the formulations of any one of embodiments 51 to 56, wherein:

(i) the first formulation comprises 0.1-20 mg/ml fibrinogen; the second formulation comprises 1-40 U/ml thrombin; and the medicament or formulations comprise a total of 5-40% (v/v) platelet lysate; or (ii) the first formulation comprises 0.1-15 mg/ml fibrinogen; the second formulation comprises 1-30 U/ml thrombin; and the medicament or formulations comprise a total of 5-15% (v/v) platelet lysate; or (iii) the first formulation comprises 0.1-12 mg/ml fibrinogen; the second formulation comprises 1-25 U/ml thrombin; and the medicament or formulations comprise a total of 7-14% (v/v) platelet lysate; or (iv) the first formulation comprises 0.2-10 mg/ml fibrinogen; the second formulation comprises 2-20 U/ml thrombin; and the medicament or formulations comprise a total of 8-12% (v/v) platelet lysate.

Embodiment 58. The use of any one of embodiments 48 to 50, or 54 to 56, or the formulations of any one of embodiments 51 to 56, wherein:
(i) the first formulation comprises less than 1 mg/ml (e.g. about 0.4 mg/ml) fibrinogen; the second formulation comprises 0.5-20 U/ml (e.g. about 1 U/ml, about 10 U/ml, about 20 U/ml) thrombin; and the medicament or formulations comprise a total of 5-40% (v/v) (e.g. about 20% (v/v)) platelet lysate; or
(ii) the first formulation comprises 1-8 mg/ml (e.g. about 4 mg/ml) fibrinogen; the second formulation comprises 0.5-20 U/ml (e.g. about 1 U/ml, about 10 U/ml, about 20 U/ml) thrombin; and the medicament or formulations comprise a total of 5-40% (v/v) (e.g. about 20% (v/v)) platelet lysate; or
(iii) the first formulation comprises 5-15 mg/ml (e.g. about 10 mg/ml); the second formulation comprises 0.5-20 U/ml (e.g. about 1 U/ml, about 10 U/ml, about 20 U/ml) thrombin; and the medicament or formulations comprise a total of 5-40% (v/v) (e.g. about 20% (v/v)) platelet lysate.

Embodiment 59. The use of any one of embodiments 48 to 50, or 54 to 56, or the formulations of any one of embodiments 51 to 56, wherein:
(i) the first formulation comprises about 0.4 mg/ml fibrinogen, and
the second formulation comprises about 2 U/ml, about 10 U/ml or about 20 U/ml thrombin, and
the medicament or formulations comprise a total of about 20% (v/v) platelet lysate; or
(ii) the first formulation comprises about 4 mg/ml fibrinogen, and
the second formulation comprises about 2 U/ml, about 10 U/ml or about 20 U/ml thrombin, and
the medicament or formulations comprise a total of about 20% (v/v) platelet lysate; or
(iii) the first formulation comprises about 10 mg/ml fibrinogen, and
the second formulation comprises about 2 U/ml, about 10 U/ml or about 20 U/ml thrombin, and
the medicament or formulations comprise a total of about 20% (v/v) platelet lysate.

Embodiment 60. The use of any one of embodiments 48 to 50, or 54 to 56, or the formulations of any one of embodiments 51 to 56, wherein when the medicament or formulations comprise:
(i) at least 0.2 mg/ml fibrinogen, at least 1 unit/mL thrombin, and about 10% (v/v) platelet lysate; or
(ii) about 10% (v/v) platelet lysate, about 2 mg/mL fibrinogen, and about 5 U/mL thrombin.

Embodiment 61. The use of any one of embodiments 48 to 50, or 54 to 56, or the formulations of any one of embodiments 46 to 51, wherein:
the first formulation and the second formulation are of equal volume, or less than: 1%, 2%, 3%, 4%, 5%, 10%, 15%, 20%, 25%, different in volume.

Embodiment 62. The use of any one of embodiments 45, 48 to 50, or 54 to 61, the formulations of any one of embodiments 51 to 61, or method of embodiment 46, or the composition of embodiment 47, wherein the tissue is eye tissue (e.g. cornea tissue).

Embodiment 63. The use of any one of embodiments 45, 48 to 50, or 54 to 61, the formulations of any one of embodiments 51 to 61, or method of embodiment 46, or the composition of embodiment 47, wherein the tissue comprises a wound or is eye tissue comprising a wound (e.g. cornea tissue comprising a wound).

Embodiment 64. The use of any one of embodiments 45, or 54 to 62, wherein the formulation is applied to the tissue of the subject using three-dimensional (3D) bioprinting.

Embodiment 65. The use of any one of embodiments 48 to 50, or 54 to 62, wherein the medicament for treating the tissue of the subject using three-dimensional (3D) bioprinting.

Embodiment 66. The method of embodiment 46, wherein the composition is applied to the tissue using three-dimensional (3D) bioprinting.

Embodiment 67. The composition of embodiment 47, wherein said treating of the tissue utilises three-dimensional (3D) bioprinting.

Embodiment 68. The formulations of any one of embodiments 51 to 62, wherein said treating of the tissue utilises three-dimensional (3D) bioprinting.

Definitions

As used in this application, the singular form "a", "an" and "the" include plural references unless the context clearly dictates otherwise. For example, the term "component" also includes a plurality of the components.

As used herein, the term "comprising" means "including". Variations of the word "comprising", such as "comprise" and "comprises," have correspondingly varied meanings. Thus, for example, a composition "comprising" component 'A' may consist exclusively of component A or may include one or more additional components (e.g. component 'B' and/or component 'C').

As used herein, the term "subject" includes any animal of economic, social or research importance including bovine, equine, ovine, primate, avian and rodent species. Hence, a "subject" may be a mammal such as, for example, a human, or a non-human mammal.

As used herein, the term "tissue" will be understood to encompass both cells that are component/s of the tissue and organ/s formed from the tissue.

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits. A "fragmented kit" refers to a delivery system comprising two or more separate containers that each contains a sub-portion of the total kit components. The containers may be delivered to the intended recipient together or separately. Any delivery system comprising two or more separate containers that each contains a sub-portion of the total kit components are included within the meaning of the term "fragmented kit". A "combined kit" refers to a delivery system containing all of the components of a reaction assay in a single container (e.g. in a single box housing each of the desired components).

As used herein, the term "about" when used in reference to a recited numerical value includes the recited numerical value and numerical values within plus or minus ten percent of the recited value.

Any description of prior art documents herein, or statements herein derived from or based on those documents, is not an admission that the documents or derived statements are part of the common general knowledge of the relevant art.

For the purposes of description, all documents referred to herein are hereby incorporated by reference in their entirety unless otherwise stated.

BRIEF DESCRIPTION OF THE DRAWINGS

Preferred embodiments of the present invention will now be described by way of example only, with reference to the accompanying figures wherein.

Figure 1:
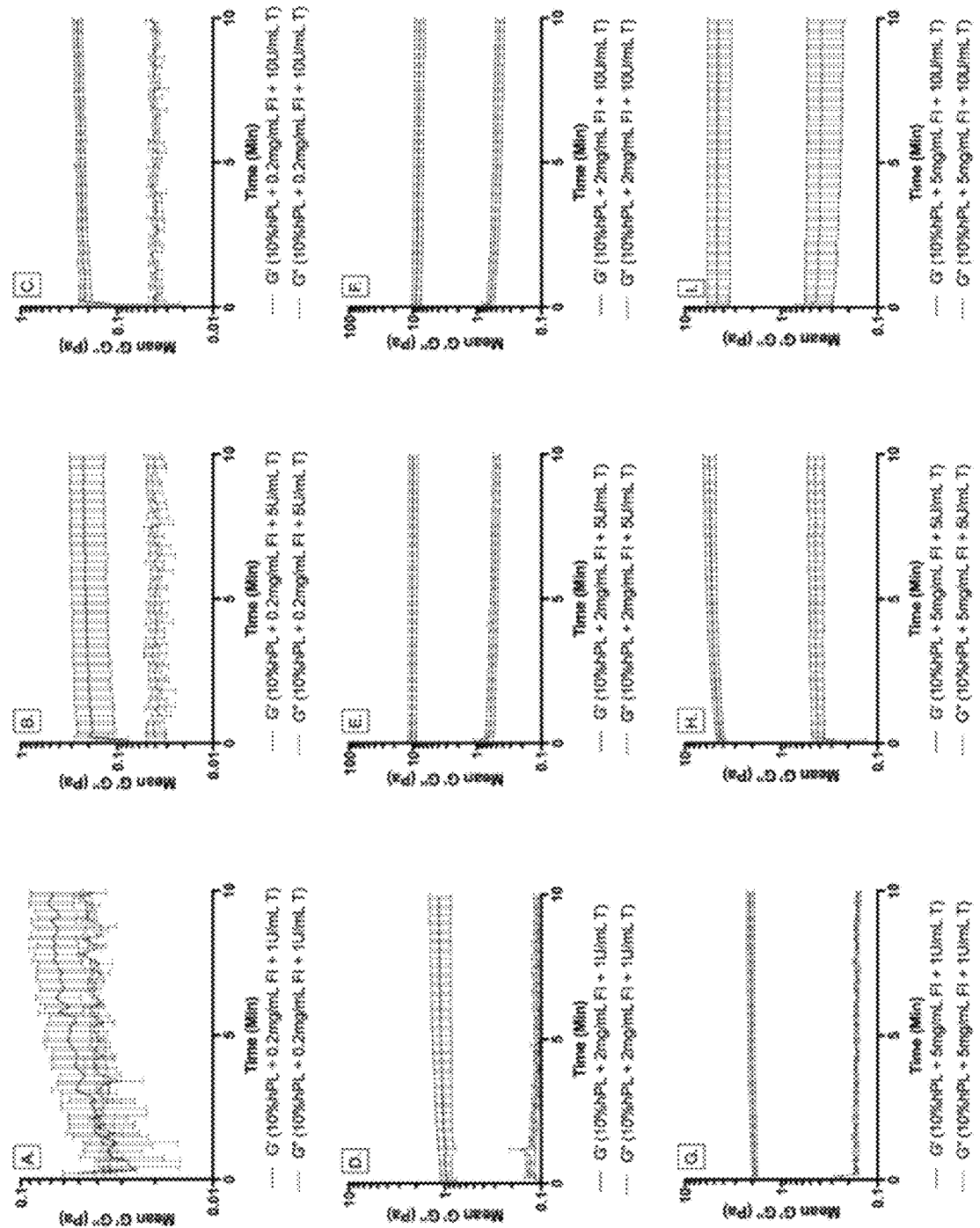
FIG. 1 is a series of graphs showing storage (G') and loss (G") moduli of compositions according to embodiments of the present invention over a time-sweep oscillation of 1 Hz at 34° C. for 10 minutes for (A) Bioink 1 (B) Bioink 2 (C) Bioink 3 (D) Bioink 4 (E) Bioink 5 (F) Bioink 6 (G) Bioink 7 (H) Bioink 8 (I) Bioink 9 (refer to table 3).

| FIG. 1 legend: |
|---|
| A. |
| G'(10% hPL + 0.2 mg/mL Fl + 1 U/mL T) |
| G"(10% hPL + 0.2 mg/mL Fl + 1 U/mL T) |
| B. |
| G'(10% hPL + 0.2 mg/mL Fl + 5 U/mL T) |
| G"(10% hPL + 0.2 mg/mL Fl + 5 U/mL T) |
| C. |
| G'(10% hPL + 0.2 mg/mL Fl + 10 U/mL T) |
| G"(10% hPL + 0.2 mg/mL Fl + 10 U/mL T) |
| D. |
| G'(10% hPL + 2 mg/mL Fl + 1 U/mL T) |
| G"(10% hPL + 2 mg/mL Fl + 1 U/mL T) |
| E. |
| G'(10% hPL + 2 mg/mL Fl + 5 U/mL T) |
| G"(10% hPL + 2 mg/mL Fl + 5 U/mL T) |
| F. |
| G'(10% hPL + 2 mg/mL Fl + 10 U/mL T) |
| G"(10% hPL + 2 mg/mL Fl + 10 U/mL T) |
| H. |
| G'(10% hPL + 5 mg/mL Fl + 1 U/mL T) |
| G"(10% hPL + 5 mg/mL Fl + 1 U/mL T) |
| I. |
| G'(10% hPL + 5 mg/mL Fl + 5 U/mL T) |
| G"(10% hPL + 5 mg/mL Fl + 5 U/mL T) |
| J. |
| G'(10% hPL + 5 mg/mL Fl + 10 U/mL T) |
| G"(10% hPL + 5 mg/mL Fl + 10 U/mL T) |

Figure 2:
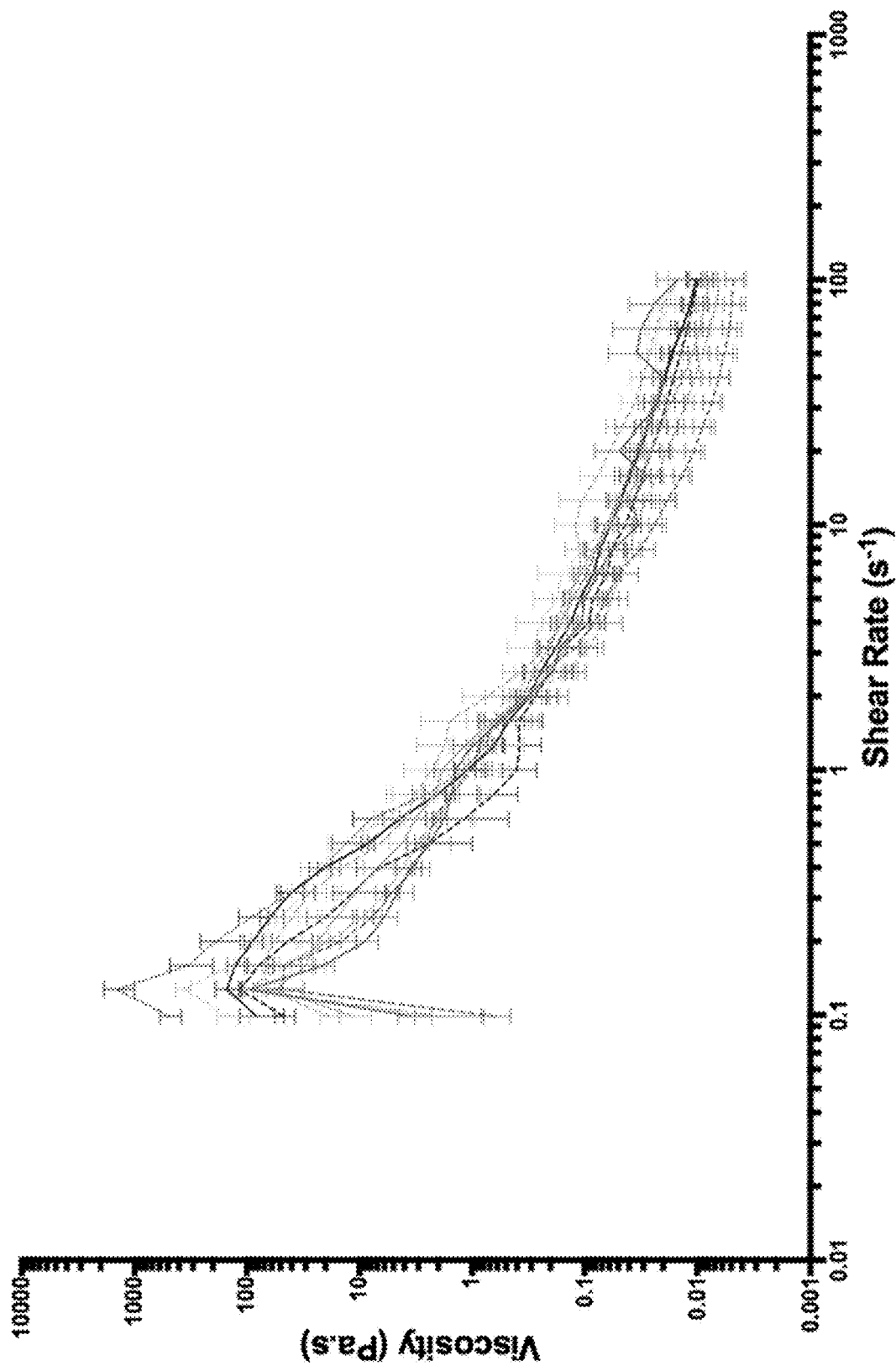

FIG. 2 provides a graph showing the viscosity of compositions according to embodiments of the present invention as measured in Pascal seconds over a shear rate ramp between $0.1\ s^{-1}$ and $100\ s^{-1}$ at a fixed temperature of 34° C. for bioink formulations 1-9 (refer to Table 3).

FIG. 2 legend:

10% hPL+2 mg/mL FI+5 U/mL T

10% hPL+0.2 mg/mL FI+1 U/mL T —10% hPL+2 mg/mL FI+10 U/mL T

10% hPL+0.2 mg/mL FI+5 U/mL T —10% hPL+5 mg/mL FI+1 U/mL T

10% hPL+0.2 mg/mL FI+10 U/mL T —10% hPL+5 mg/mL FI+5 U/mL T

10% hPL+2 mg/mL FI+1 U/mL T —10% hPL+5 mg/mL FI+10 U/mL T

Figure 3:
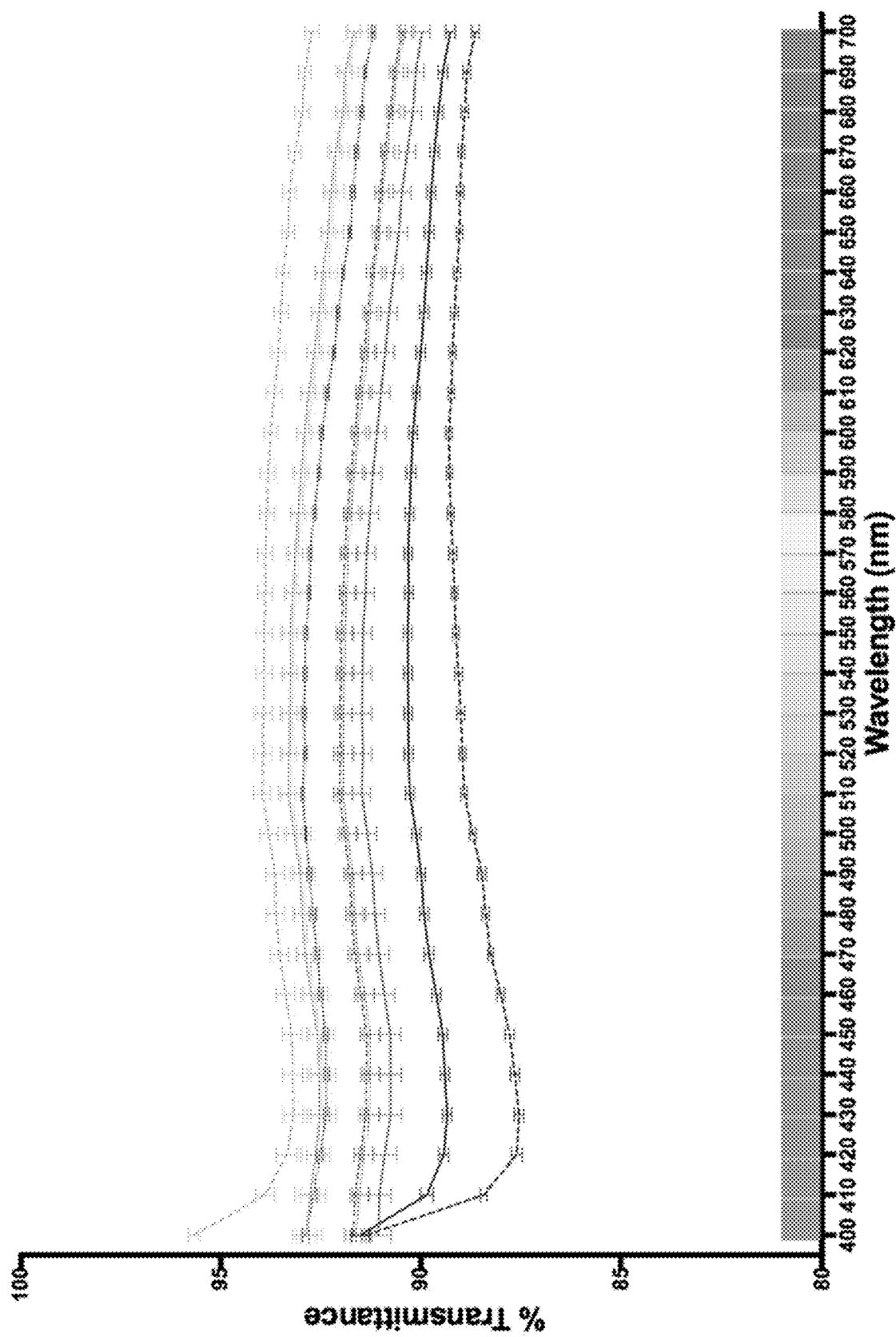

FIG. 3 shows a graph indicating the mean percentage transmittance of compositions according to embodiments of the present invention across wavelengths of the visible spectrum (400-700 nm) for bioink formulations 1-9 (refer to Table 3).

FIG. 3 legend:

10% hPL+2 mg/mL FI+5 U/mL T

10% hPL+0.2 mg/mL FI+1 U/mL T —10% hPL+2 mg/mL FI+10 U/mL T

10% hPL+0.2 mg/mL FI+5 U/mL T —10% hPL+5 mg/mL FI+1 U/mL T

10% hPL+0.2 mg/mL FI+10 U/mL T —10% hPL+5 mg/mL FI+5 U/mL T

10% hPL+2 mg/mL FI+1 U/mL T —10% hPL+5 mg/mL FI+10 U/mL T

Figure 4:
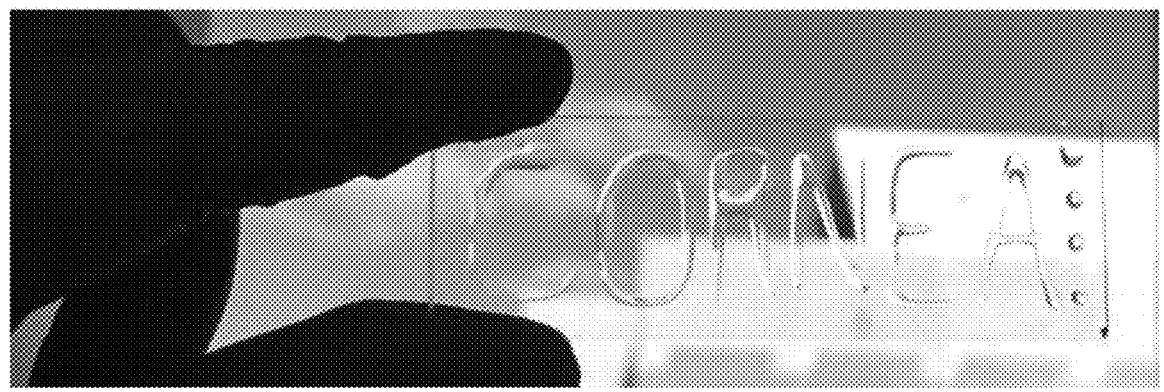

FIG. 4 is an image of a composition according to an embodiment of the present invention bioink 5 (refer to Table 3) adhered to a glass slide.

Figure 5:
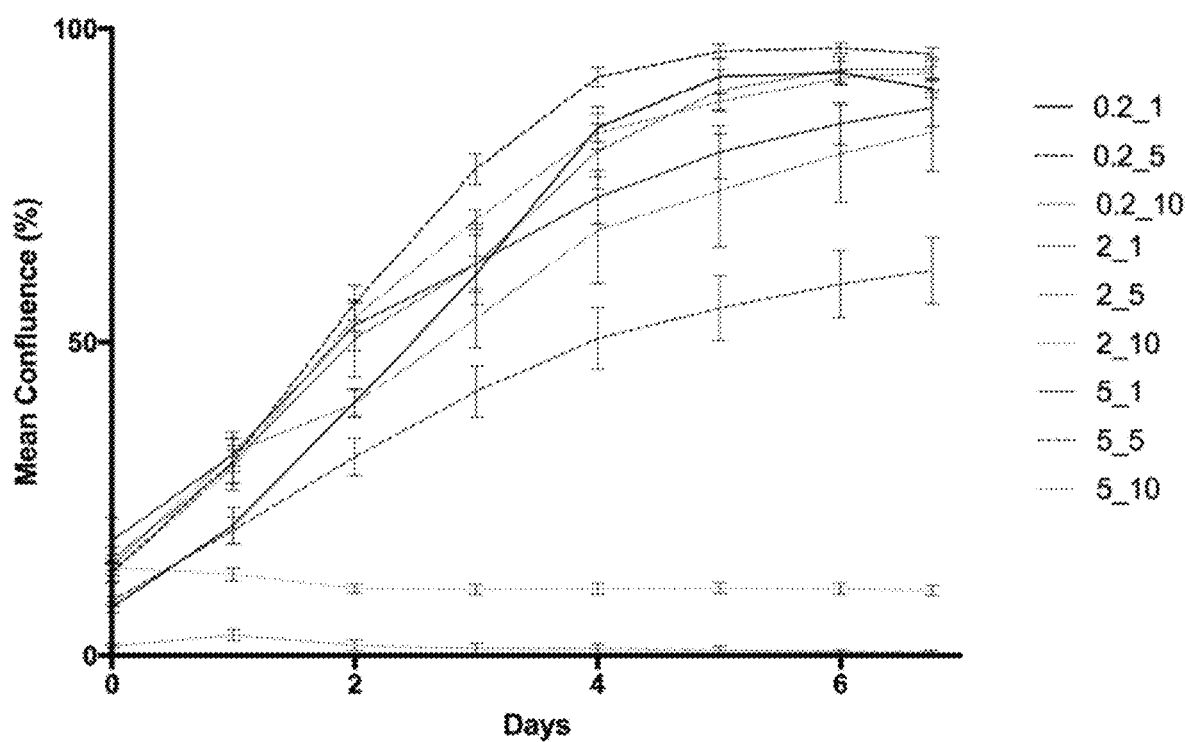

FIG. 5 provides a graph showing the mean confluence of HCE-T cells over time (n=6 per condition) as measured via Incucyte Zoom for bioinks 1-9 (refer to Table 3).

FIG. 5 legend:

0.2_1
0.2_5
0.2_10
2_1
2_5
2_10
5_1
5_5
5_10

Figure 6:
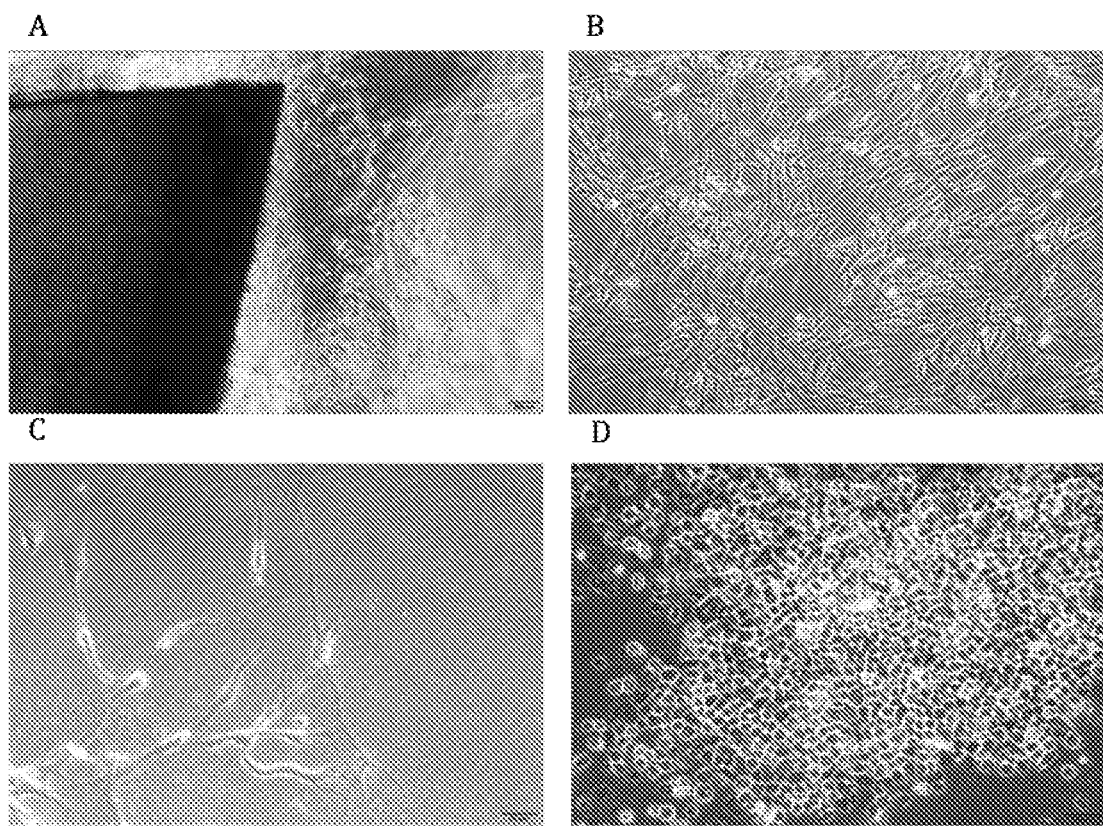

FIG. 6 provides a series of images showing primary human corneal cells cultured and growth in bioink 5 (Table 3). (A) demonstrates corneal epithelial cells proliferating out of a corneal explant. (B) demonstrates keratocytes growth. (C) demonstrates corneal neurons growth. (D) demonstrates corneal endothelial cells growth.

Figure 7:
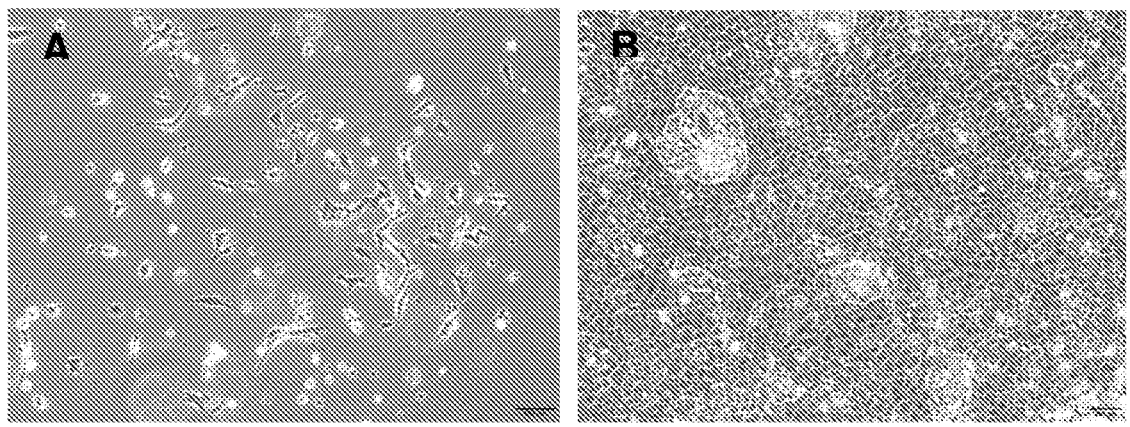

FIG. 7 provides images demonstrating the successful growth of SHSY-5Y in a bioink formulation according to an embodiment of the present invention bioink 5 (table 3). (A) demonstrates cells growth in the ink. (B) demonstrates the cells reaching full confluency in the ink.

Figure 8:
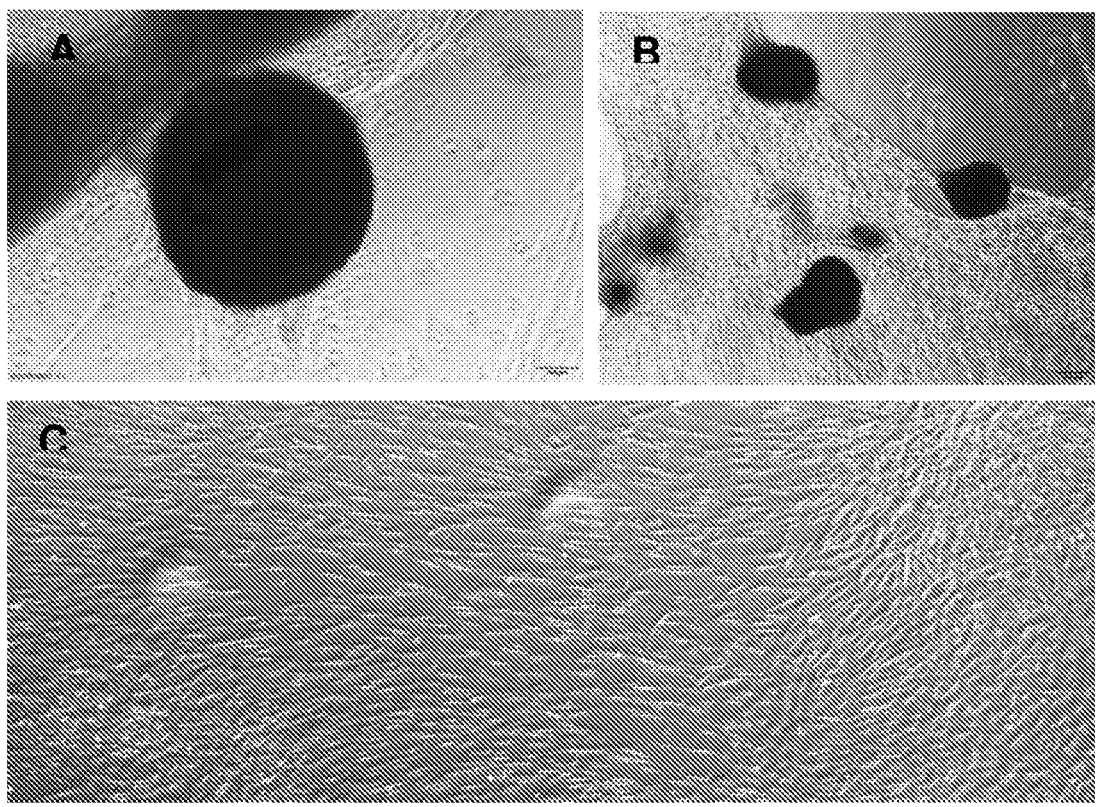

FIG. 8 shows images of spheroid aggregates cultured in a bioink formulation according to an embodiment of the present invention (A and B). (C) shows corneal keratocytes that grew from a spheroid aggregate.

Figure 9:
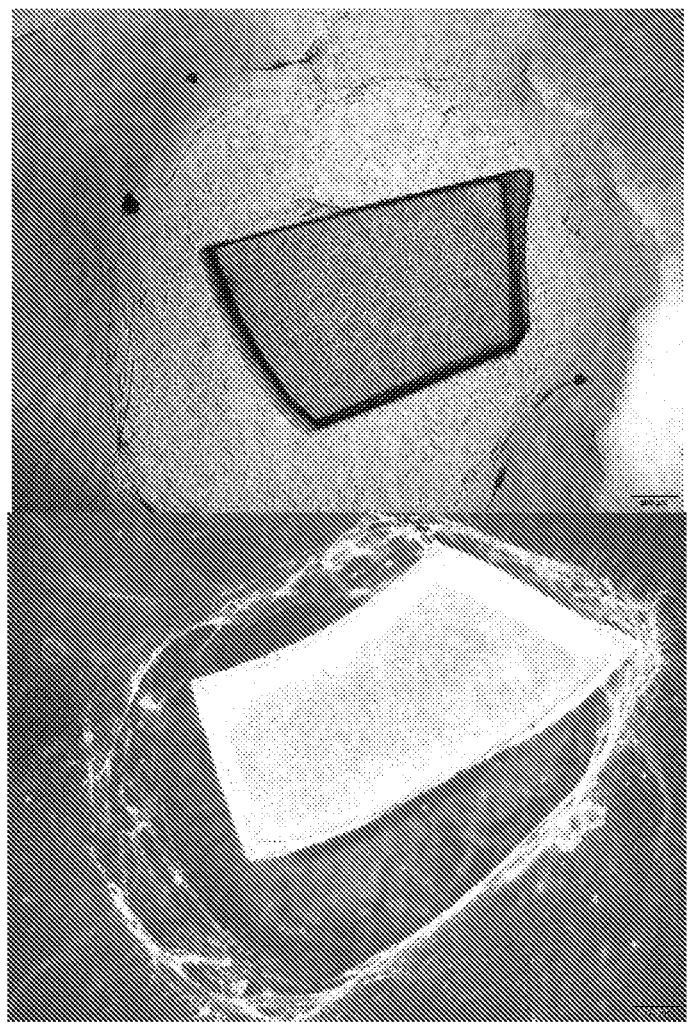

FIG. 9 provides images of absorption and degradation of a composition according to an embodiment of the present invention bioink 5 (table 3) via resorption over 2 to 7 days.

Figure 10:
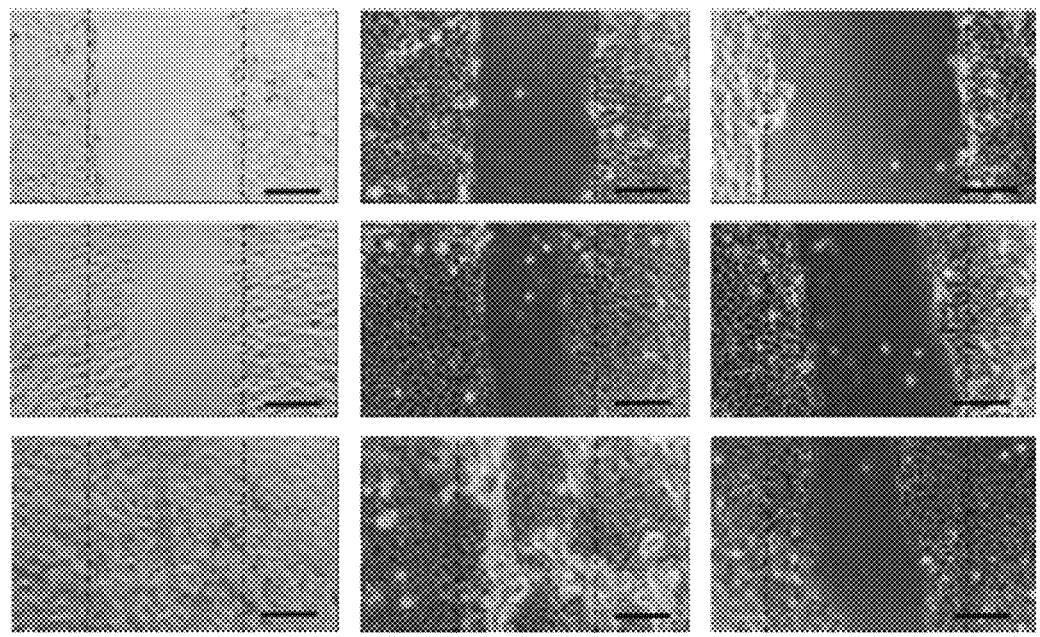
Figure 10:
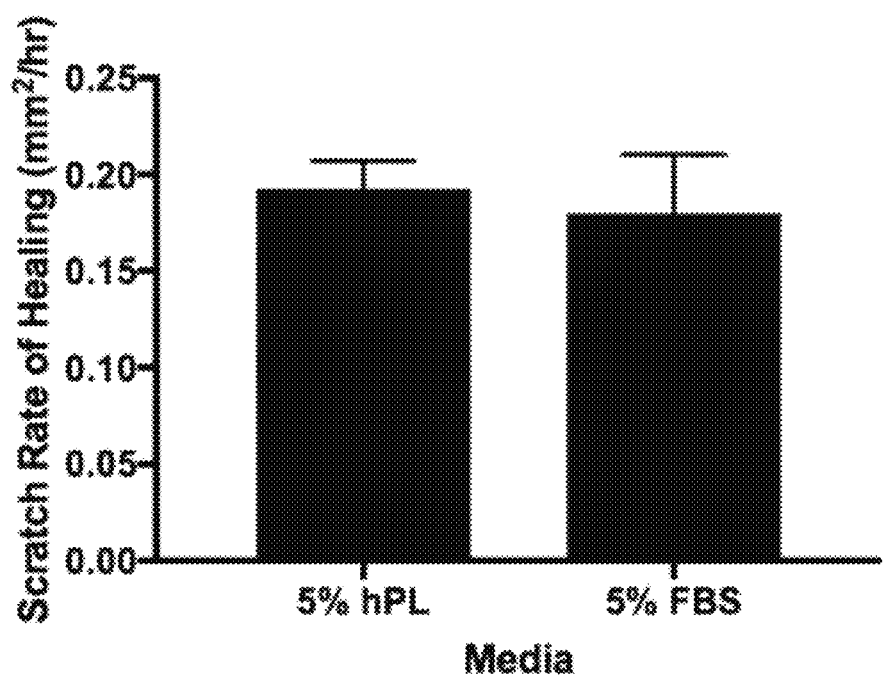

FIG. 10 provides images (A) and a graph (B) showing the results of scratch assays of HCE-T cells (n=3 for each condition) in 5% human platelet lysate (hPL), 5% foetal bovine serum (FBS) and DMEM only. Wound closure was not observed in the DMEM only condition. (A) demonstrates a representation of wound closure at 0, 5 and 24 hours (top row 0 hr; middle row 5 hr; lower row 24 hr; left column 5% hPL; middle column 5% FBS; right column DMEM only). (B) demonstrates the rate at which scratch healing was observed±SEM for the 5% hPL condition (0.19±0.01 μm/hr) and the 5% FBS condition (0.18±0.03). No significant difference was found in rate of healing between 5% FBS and 5% hPL (p>0.05).

Figure 11:
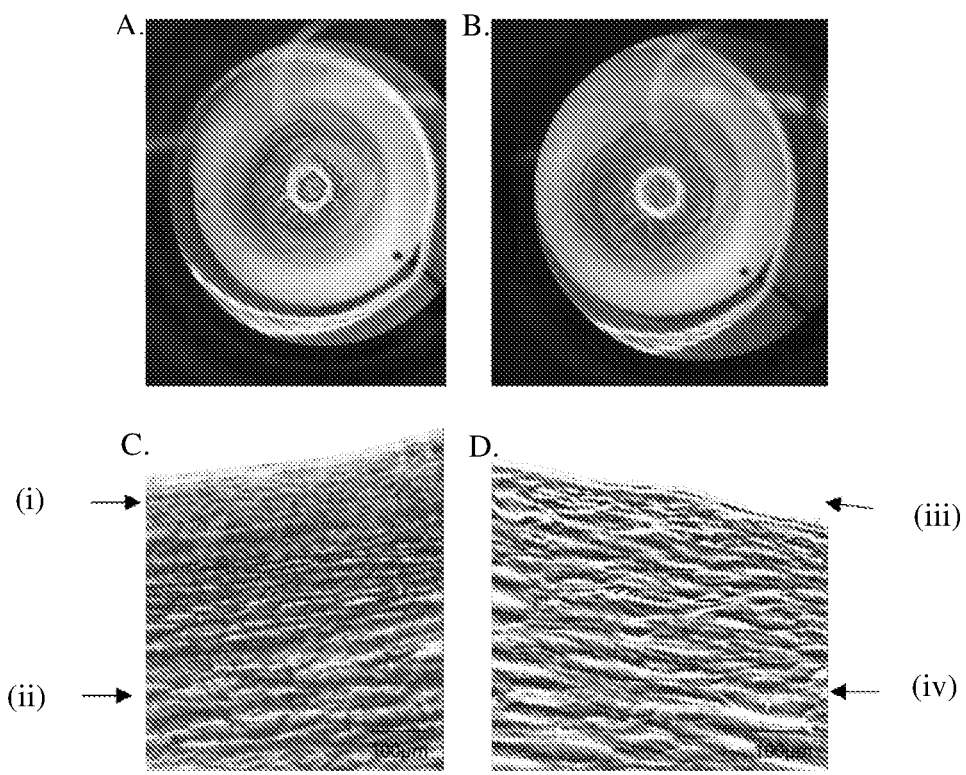
Figure 12:
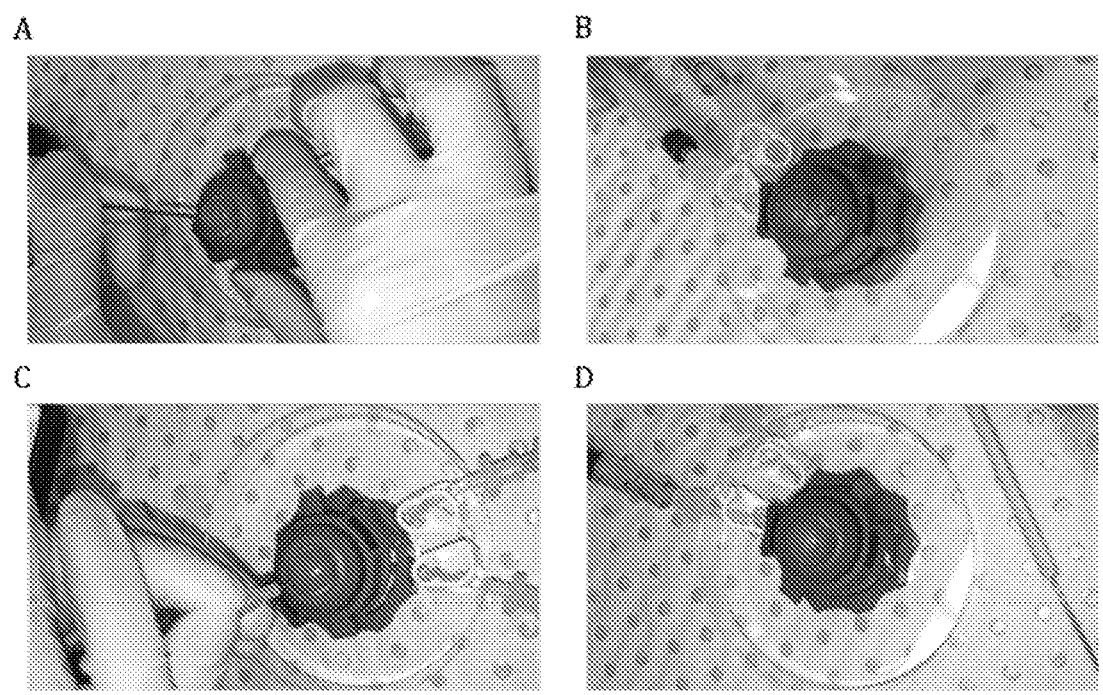

FIG. 11 provides images showing the re-epithelialisation of an ex vivo, ulcerated, human cornea that had been previously rejected for transplant use. Bioink was applied at day 1 and 4 and fixed, cryosectioned and stained with H&E at day 7. (A) demonstrates the initial ulcer, with the ulcerated regions emphasised in red. (B) demonstrates the size of the epithelial-free surface post wound-debriding. (C) demonstrates H&E staining of the central part of the cornea and shows complete re-epithelialisation with a thickness and morphology comparable to that of a healthy human cornea. (D) demonstrates H&E staining of the central part of a de-epithelialised cornea for comparison. (i): epithelium; (ii): stroma; (iii): absent epithelium; (iv): stroma FIG. 12 provides images demonstrating the creation and successful sealing of a perforation (1 cm in diameter) on a post-mortem porcine cornea. (A) depicts perforation creation. (B) depicts the leaking cornea. (C) depicts the application of the bioink with an applicator device. (D) depicts a sealed perforation 2 minutes post bioink application.

Figure 13:
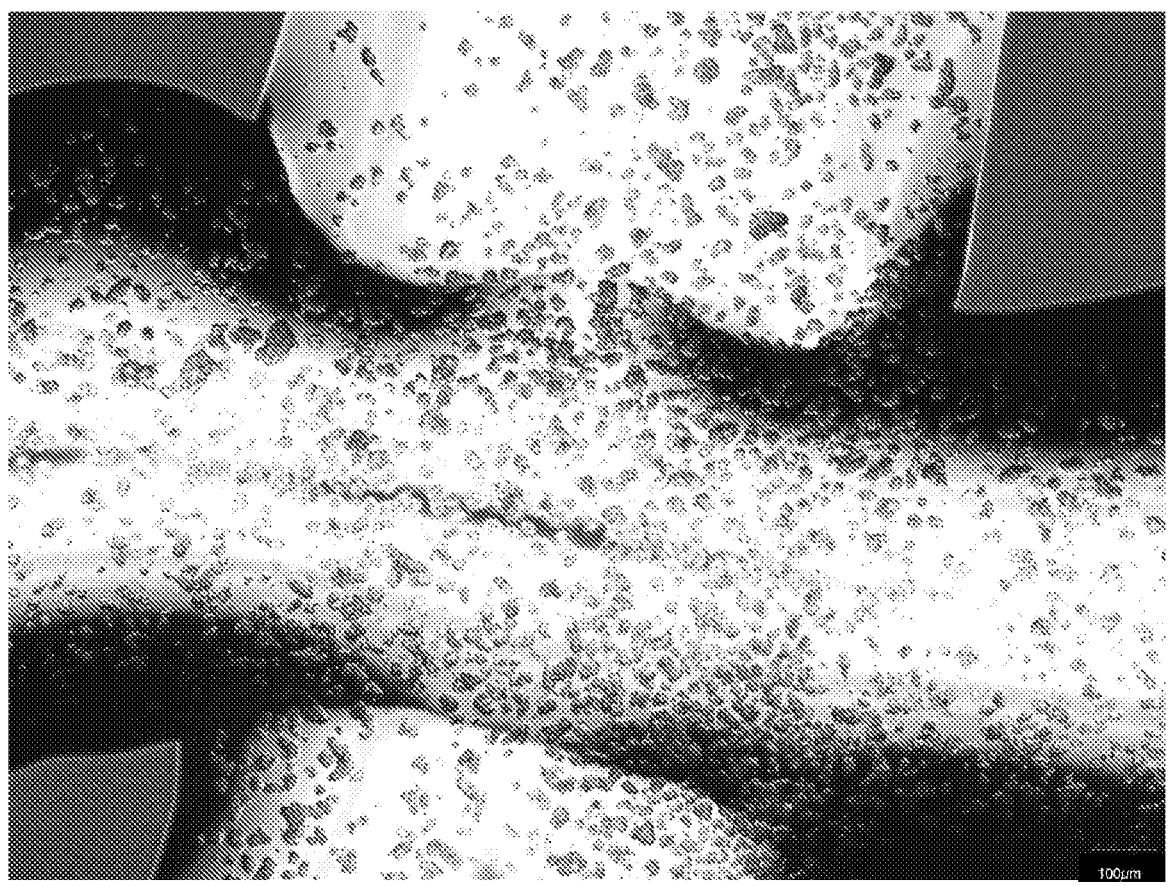

FIG. 13 provides an image demonstrating the printing of a bioink of the present invention in layers.

Figure 14:
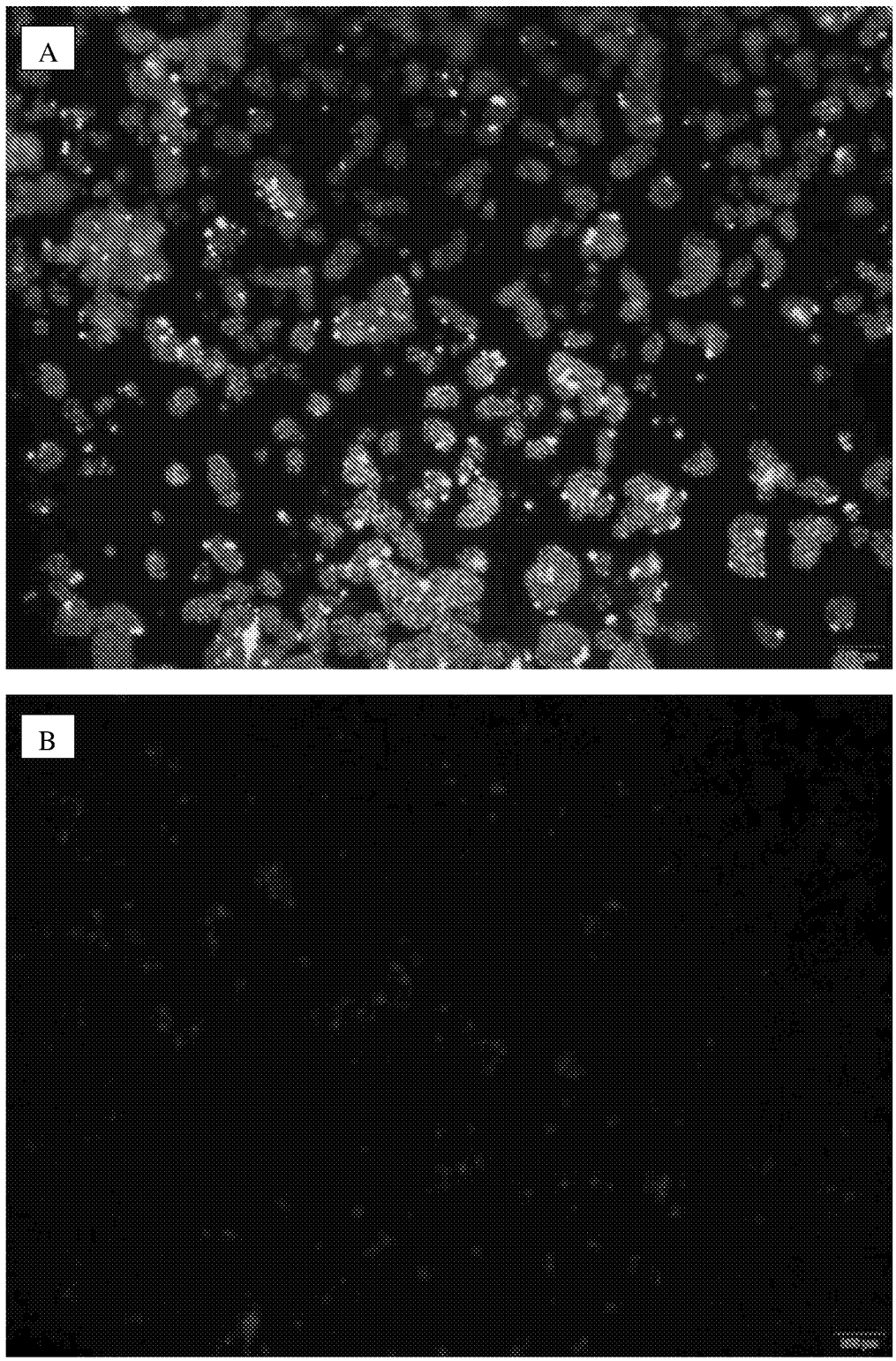
Figure 14:
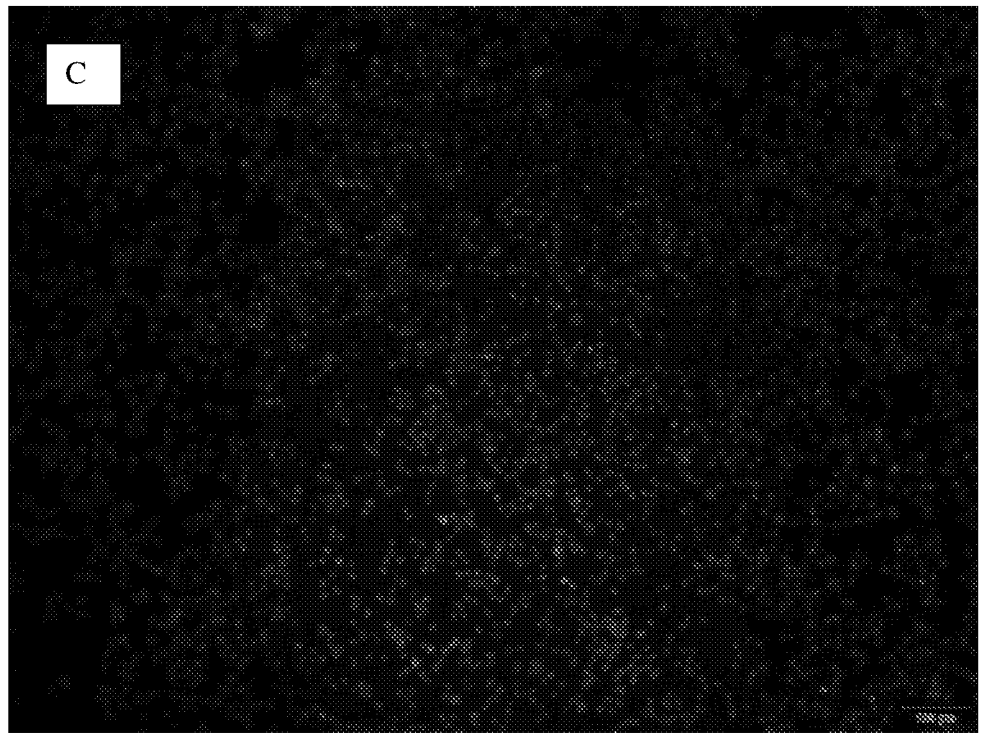
Figure 14:
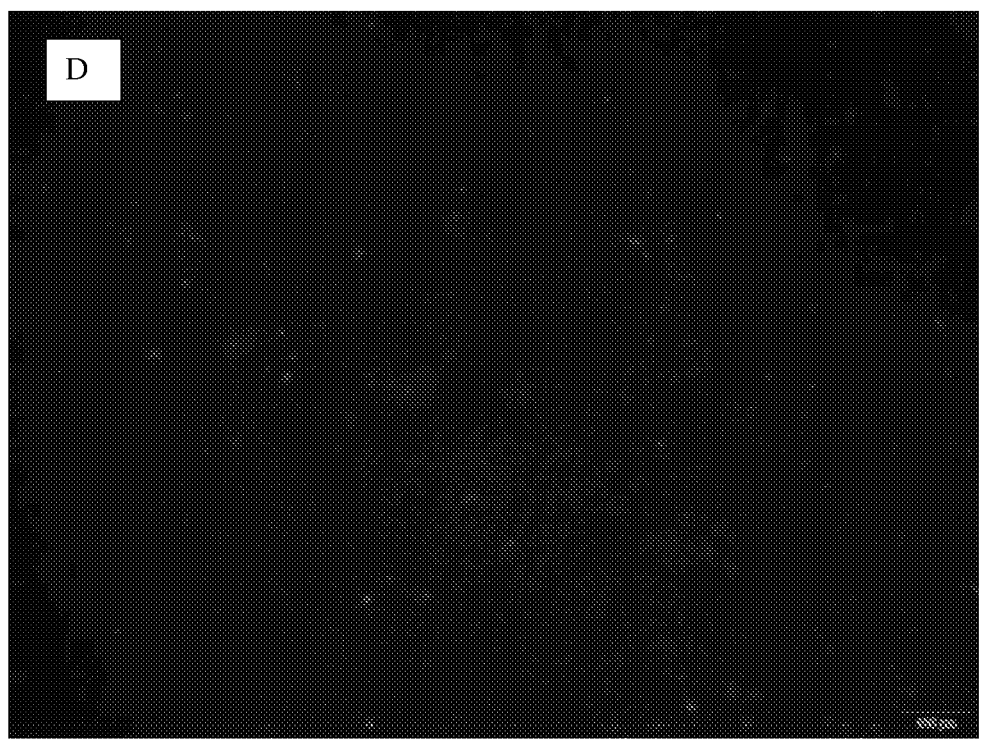

FIG. 14 shows images of a printed bioink of the present invention comprising P18 HCET cells stained with Hoescht (blue) stained or propidium iodide (red). A and B: 2 hours post extrusion; C and D: 72 hours post extrusion.

Figure 15:
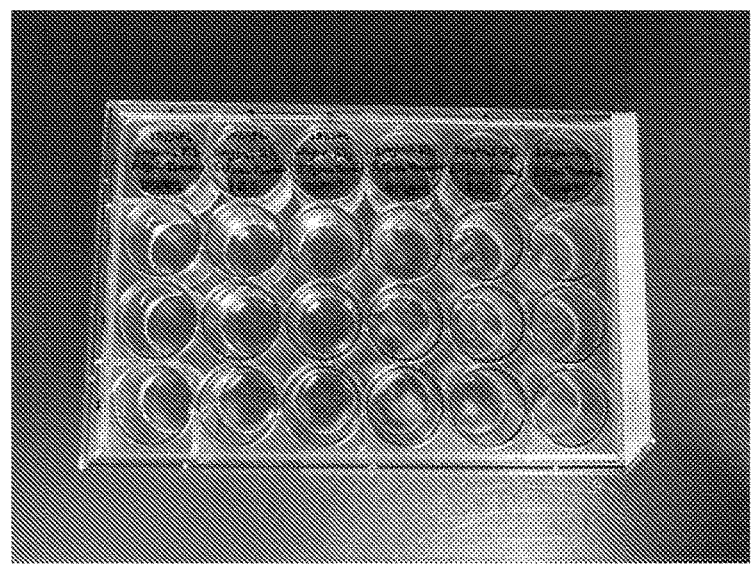

FIG. 15 shows the transparency of printed bioink compositions according to embodiments of the present invention.

Figure 16:
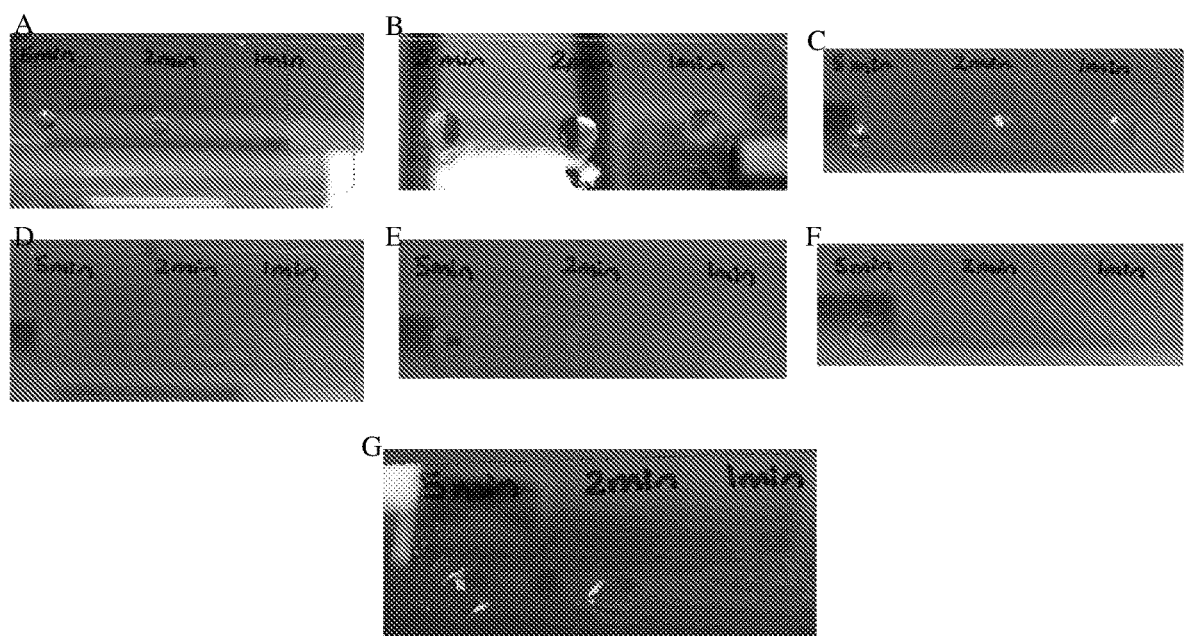

FIG. 16 shows images of bioink according to the present invention on the glass slides post dipping tests. A. shows composition 1, B. shows composition 2. C. shows composition 3, D. shows composition 4, E. shows composition 5, F. shows composition 6. E. shows composition 7 as per Table 5.

Figure 17:
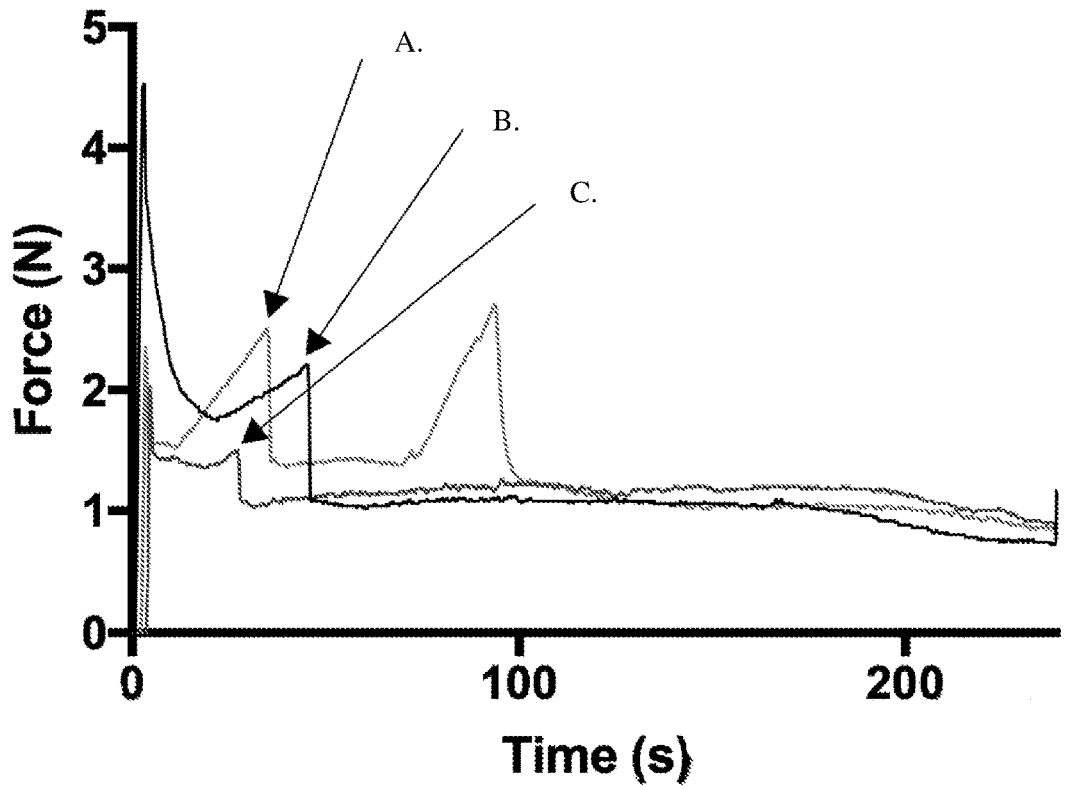

FIG. 17 is a graph showing the level of force at which human corneal wounds (1.5 mm) treated with bioink of the present invention are able to prevent leakage. A: 1.63N i.e. 112 mmHg; B. 1.33N i.e. 105 mmHG; C: –0.71N i.e. 56 mmHG.

Figure 18:
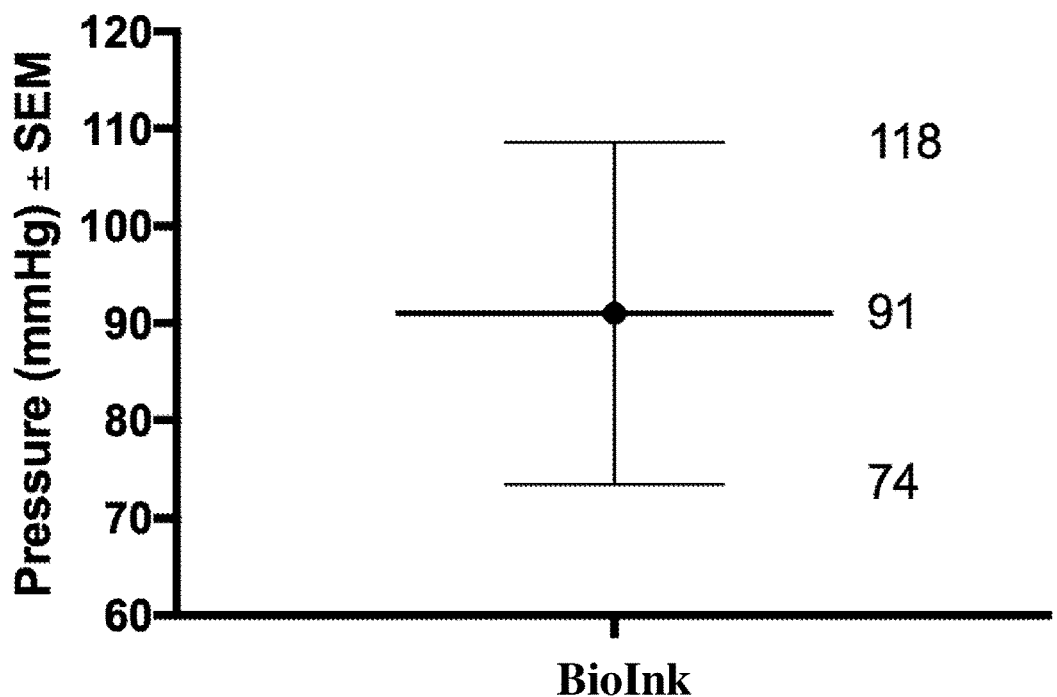

FIG. 18 is a graph showing mean burst pressure (mmHg±SEM) that bioink of the present invention is able to withstand with a 1.5 mm diameter perforation sealed with bioink.

Figure 19:
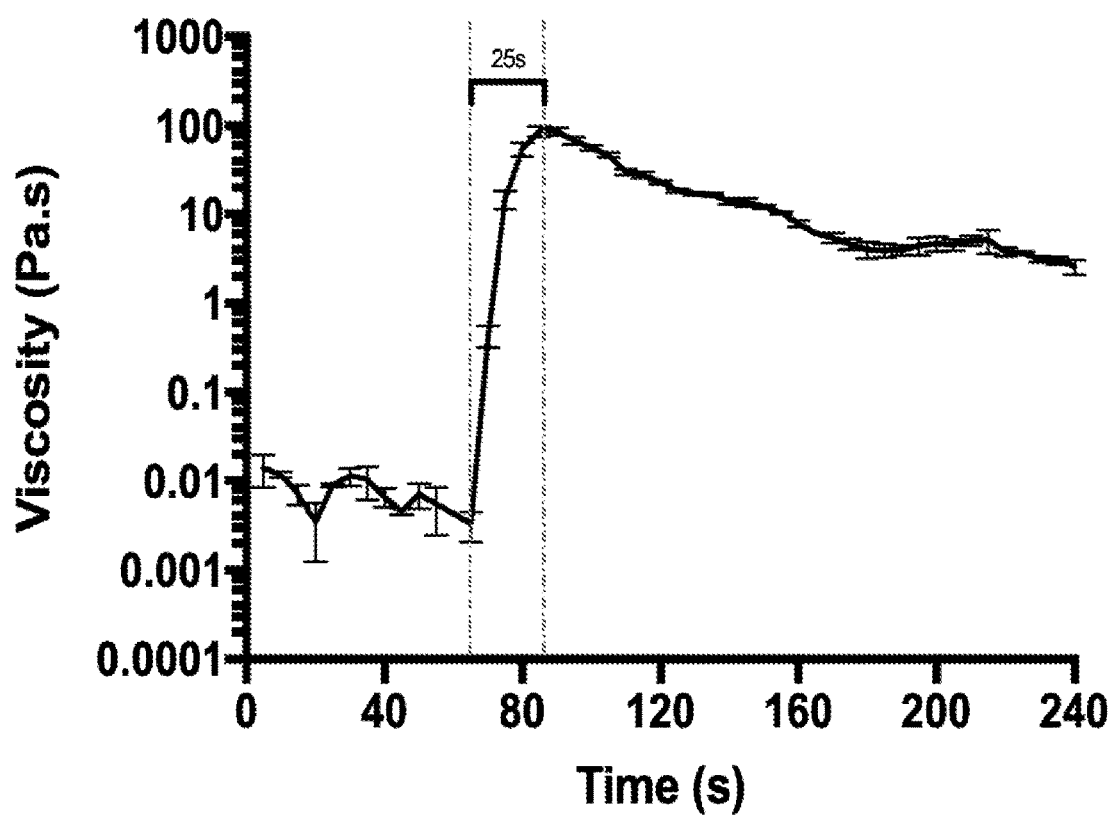

FIG. 19 is a graph showing the viscosity±SEM of bioink of the present invention at a fixed shear rate of $1\ s^{-1}$ measured in Pascal seconds (Pa·s) over time in seconds (n=3). Component B was added at t=60 s. Setting time was defined as the time taken for the viscosity to peak post addition and is denoted by the pink dotted lines. Setting time was determined to be 25 seconds at a fixed shear rate of $1\ s^{-1}$.

Figure 20:
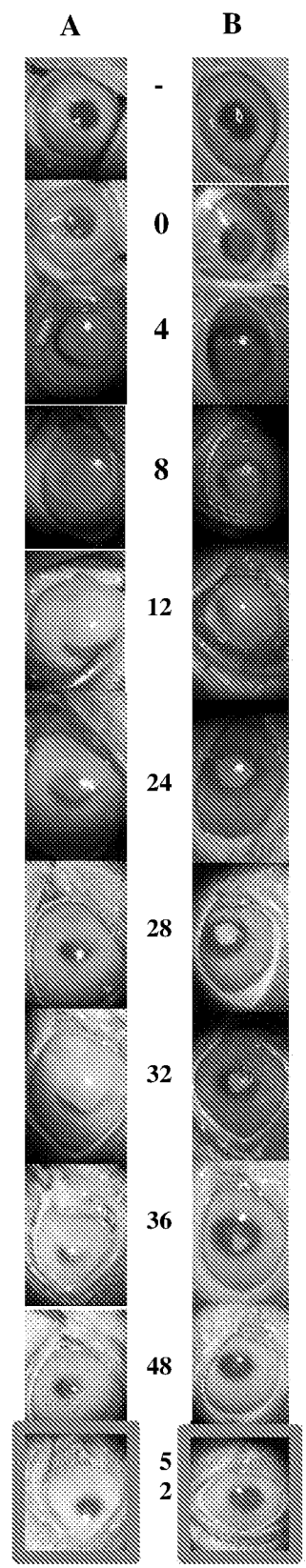

FIG. 20 provides images of wound healing over time in: (i) the eye of a rabbit with a corneal epithelial wound treated using bioink of the present invention (column B); and (ii) the eye of a control rabbit with a corneal epithelial wound treated with histoacryl (column A). Wound healing in both control and treatment rabbit was achieved at t=52 hours. – (prior to wound creation); numerals (no. of hours post wound creation).

Figure 21:
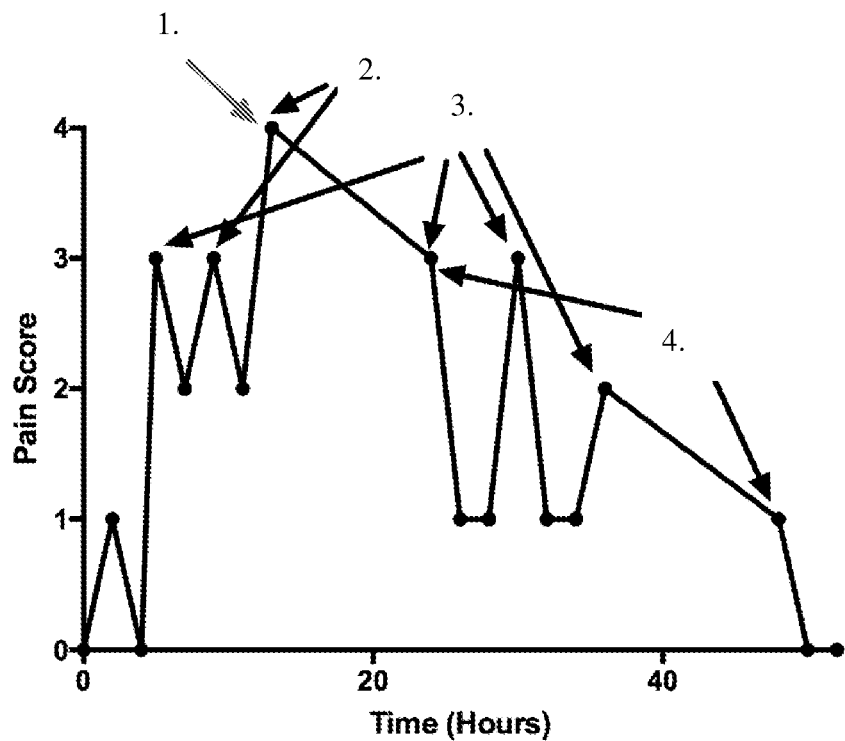

FIG. 21 is a graph depicting a pain score of the control rabbit of FIG. 20 as measured over the time until wound healing was achieved (t=52 hours). Time points where additional analgesia was administered are recorded. 1: ketamine (recue analgesia) administered; 2: methadone (rescue analgesia) administered; 3: buprenorphine (IM) administered; 4. meloxicam administered.

Figure 22:
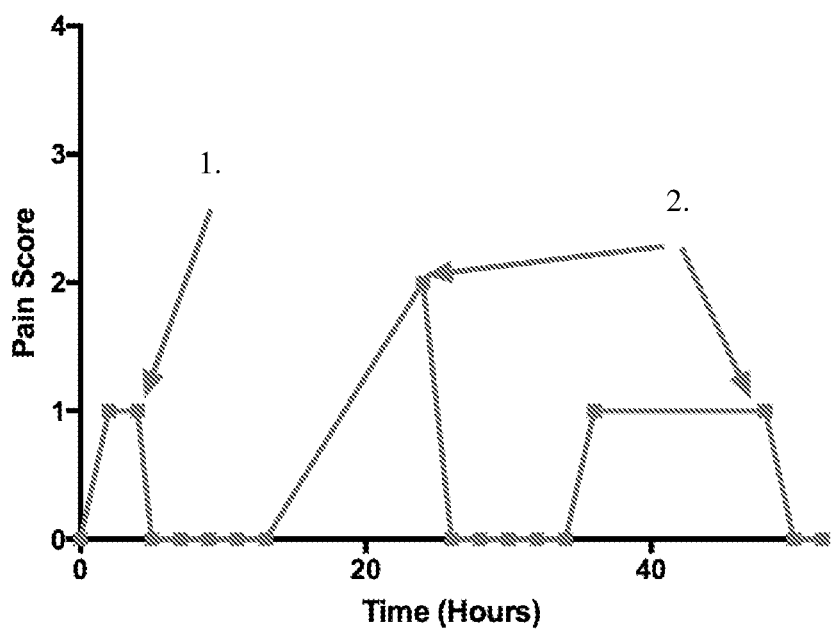

FIG. 22 is a graph depicting a pain score of the bioink-treated rabbit of FIG. 20 measured over the time until wound healing was achieved (t=52 hours). Time points where additional analgesia was administered are recorded. 1: buprenorphine (IM) administered; 2: meloxicam administered.

Figure 23:
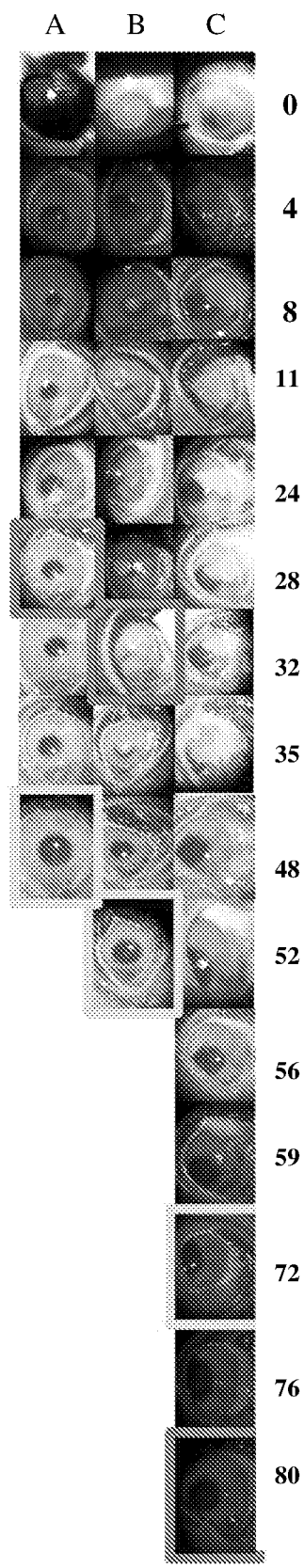

FIG. 23 provides images of wound healing over time in: (i) eyes of two rabbits each with corneal perforations treated using bioink of the present invention (columns A and B); and (ii) the eye of a control rabbit with a corneal perforation treated with histoacryl (column C). The pink border marks when corneal perforation wound healing was achieved. The green border marks when secondary ulcer formation was healed. Corneal perforation wound healing in the control rabbit was observed at t=80 hours and in the treatment rabbits at t=28 and t=32 hours respectively. A: bioink-treated rabbit 2; B: bioink-treated rabbit 2; C: control rabbit. numerals (no. of hours post wound creation).

Figure 24:
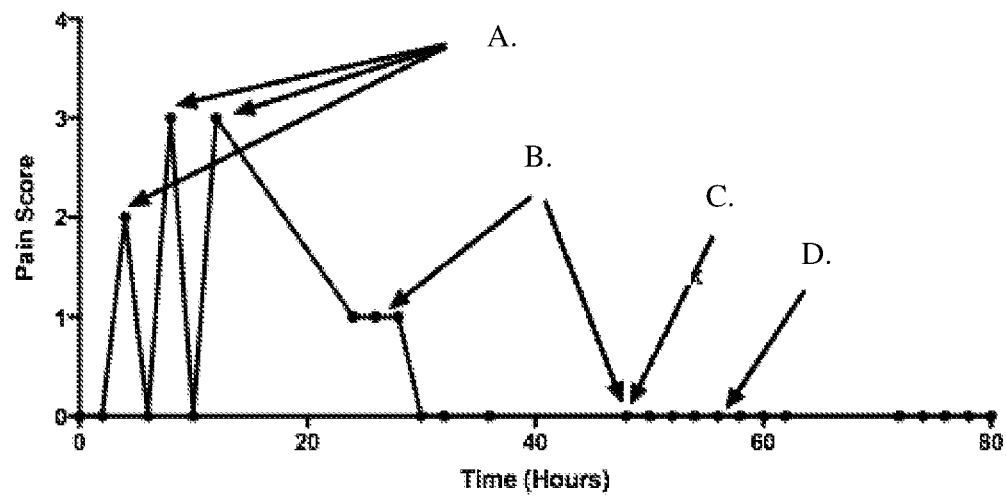

FIG. 24 is a graph depicting pain scores of the control rabbit of FIG. 23 (column C) as measured over the time until complete wound healing was achieved (t=80 hours). Time points where additional analgesia was administered are recorded. A: buprenorphine (IM) administered; B: meloxicam administered; C: histoacryl off; D: secondary ulceration formation.

Figure 25:
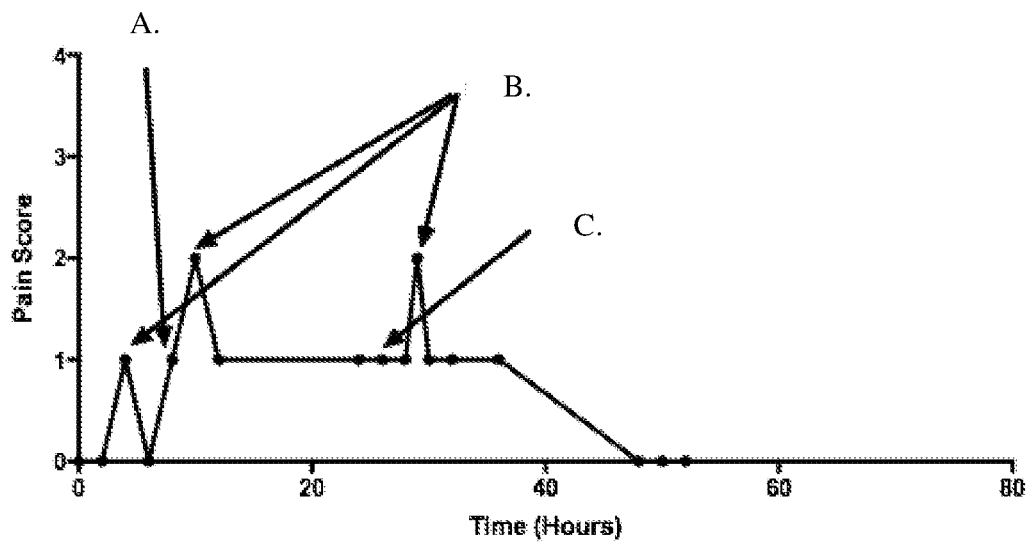

FIG. 25 is a graph depicting pain scores of the bioink-treated rabbit of FIG. 23 (column A) measured over the time until complete wound healing was achieved (t=52 hours). Time points where additional analgesia was administered are recorded. A: secondary ulceration formation; B: buprenorphine (IM) administered; meloxicam administered.

Figure 26:
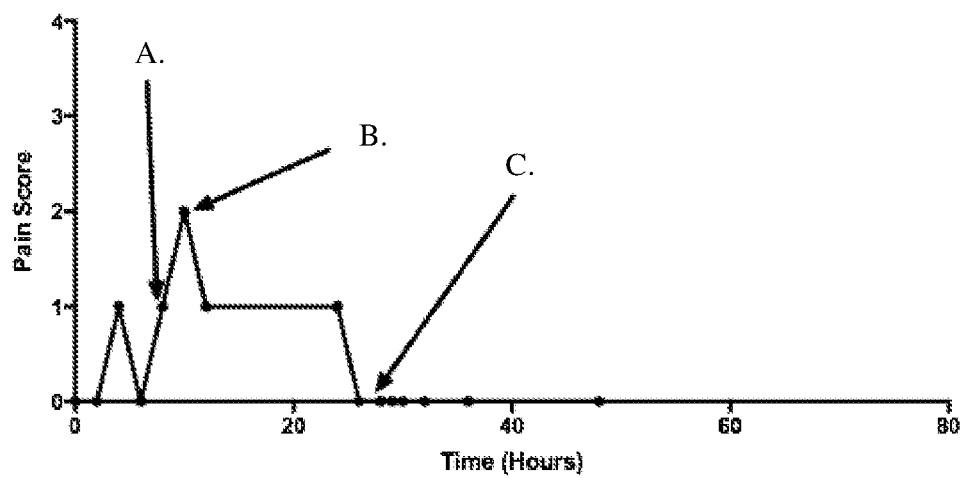

FIG. 26 is a graph depicting pain scores of the bioink-treated rabbit of FIG. 23 (column B) measured over the time until complete wound healing was achieved (t=48 hours). Time points where additional analgesia was administered are recorded. A: secondary ulceration formation; B: buprenorphine (IM) administered; meloxicam administered.

Figure 27:
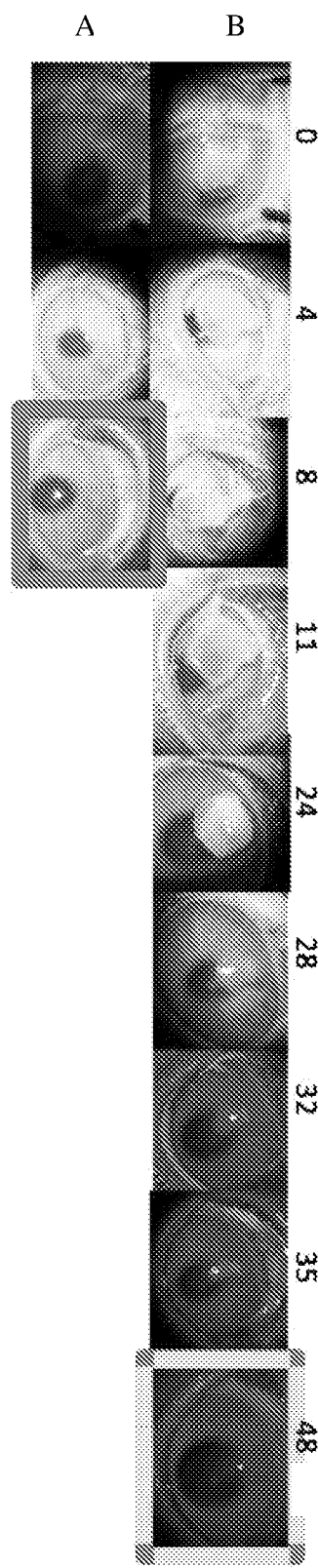

FIG. 27 provides images of wound healing over time in: (i) the eye of a rabbits with a modified corneal perforation treated using bioink of the present invention (columns A); and (ii) the eye of a control rabbit with a modified corneal perforation treated with histoacryl (column B). The pink border marks when modified corneal perforation wound healing was achieved. The green border marks when secondary ulcer formation was healed. Modified corneal perforation healing in the control rabbit was observed at t=48 hours and in the treatment rabbit at t=8 hours. Column A: bioink-treated rabbit 2; column B: control rabbit. numerals (no. of hours post wound creation).

Figure 28:
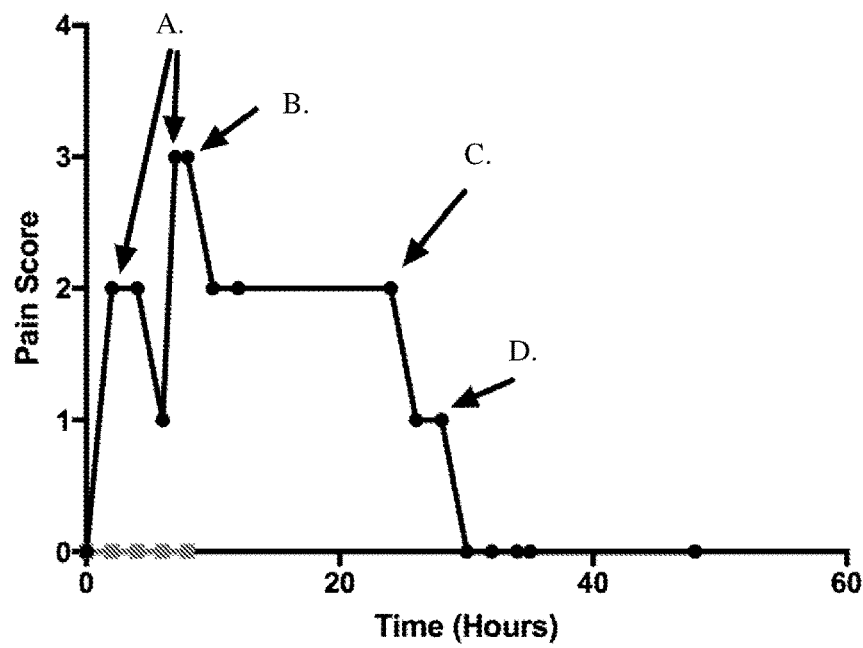
Figure 29:
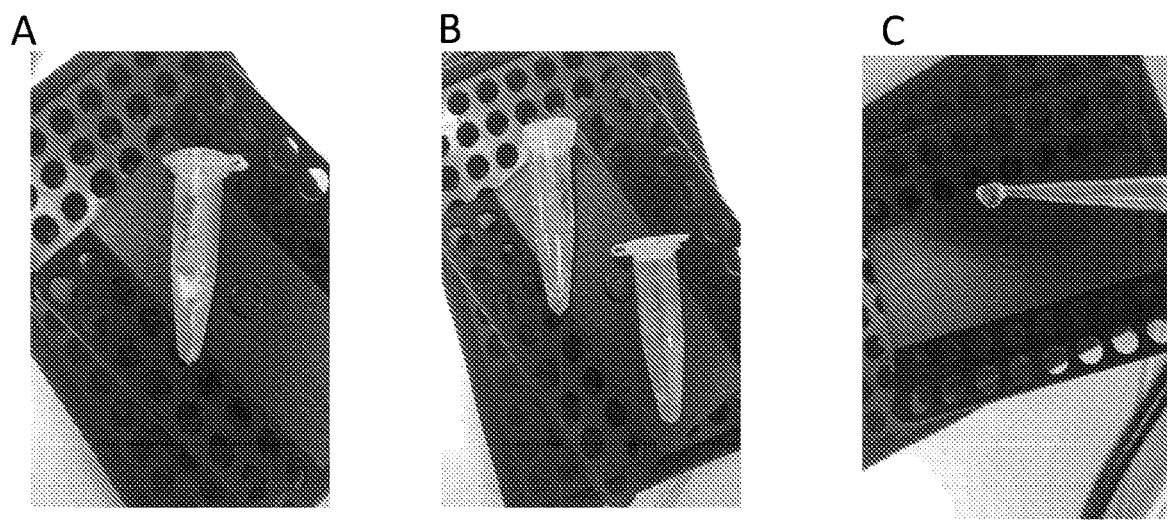

FIG. 28 is a graph depicting a pain score of: (i) the control rabbit (dark line) of FIG. 27 (column B) as measured over the time taken until complete wound healing was achieved (t=48 hours); and (ii) the bioink-treated rabbit (lighter line) of FIG. 27 (column A) measured over the time taken until complete wound healing was achieved (t=8 hours). Time points where additional analgesia was administered are recorded. No additional analgesia was administered to the bioink-treated rabbit. A: buprenorphine (IM) administered; B: methadone (rescue analgesia) administered; C: meloxicam administered; D: histoacryl off and secondary ulcer formation. FIG. 28 legend:
- Control
- Ink FIG. 29 shows images of (A) bioink samples were freeze dried at –40 degrees Celsius; (B) freeze dried samples of (A) reconstituted with 50 uL water per tube in to clear liquid; and (C) an adhesive and transparent gel formed following reconstitution.

DETAILED DESCRIPTION

The present inventors have developed platelet lysate compositions with mechanical and structural properties that facilitate application to tissue in a structured form. In particular, the compositions of the present invention may be used to apply platelet lysates to tissue (e.g. eye) using two- or three-dimensional bioprinting techniques. The compositions provide a means of delivering agents to biological targets (e.g. organs, tissues, cells). While suitable for application in the treatment of corneal injuries, the compositions described herein provide a platform for numerous treatments in the field of wound healing by virtue of providing, for example, structural support, viable cells, and other factors that facilitate the process of wound healing. There is a need in the art for effective blood-derived treatments for wounds such as ocular surface wounds. The compositions described herein are based on platelet lysate which, in the context of eye treatment, not only lubricates the ocular surface to act as a tear substitute, but also provides a source of a diverse range of growth factors and cytokines that facilitate wound healing. The compositions described herein may utilise biomaterial that mimics in vivo tissue and acts as a scaffold for cells to populate, and/or, through the manipulation of conditions encourages the cells themselves to regenerate their surrounding matrix. In the context of their suitability for application to eye tissue the present inventors have, for example, addressed the difficulties of creating a matrix that can embody the structural integrity of the tissue under treatment (e.g. cornea) whilst maintaining transparency and still being porous and biocompatible enough to allow for the infiltration, migration and/or proliferation of corneal cells and the required healing promoting growth factors. The balance between providing the nutritional needs of damaged tissue while meeting the structural, mechanical and physical requirements of damaged tissue (e.g. eye tissue such as cornea) was a problem existing at the time that the present invention arose. The present invention provides improved compositions and methods for delivering agents to a broad variety of biological targets. Without limitation to any particular application, the compositions may be used for treat wounds and other forms of tissue damage.

Compositions for Delivery of Biological Agents

The present invention provides compositions suitable for the delivery of agents to biological targets such as tissues and cells.

The compositions utilise a base scaffold material to provide structural support upon application to a biological target (e.g. tissues, membranes, cells, organs), to facilitate the delivery of agents to the biological target, and/or to promote the regeneration of damaged tissue, and/or cells within the biological target.

No particular limitation exists regarding the specific material/s used to generate the scaffolds.

For example, the scaffolds may be fibrin scaffolds. These may be generated, for example, via the use of fibrinogen and thrombin in the compositions. As known to those skilled in the art, the conversion of fibrinogen to fibrin generally occurs in three stages. Thrombin may catalyse the first stage which is a limited proteolysis to release fibrinopeptides (FpA and FpB) from fibrinogen and thereby provide fibrin monomers. In the second stage, the fibrin monomers may form intermediate polymers through noncovalent interactions. In the third stage, the intermediate polymers can aggregate to form a three-dimensional fibrin matrix. Fibrin formation and its use in biological scaffolds is described, for example, in Ahmed et al. (Tissue Eng Part B Rev. 2008 June; 14(2): 199-215).

The compositions of the present invention may further optionally comprise ions and/or a source of ions. Non limiting examples of suitable ions include calcium ions. Non limiting examples of suitable ion sources include compounds comprising calcium (e.g. calcium chloride).

The compositions of the present invention may include platelet lysate. The platelet lysate may, for example, be mammalian platelet lysate (e.g. generated using human, canine, feline, bovine, porcine, equine, caprine, hircine, murine, leporine, cricetine, or musteline platelets, or any combination thereof). The source of platelets utilised to generate the platelet lysate will generally depend on the specific purpose for which the composition is to be used. As known to those of ordinary skill in the art, platelet lysate is generated by isolating platelets, lysing them and removing cellular debris. The constituents of platelet lysate and its applications have been well analysed (see, for example, Burnouf et al. Biomaterials. 2016 January; 76:371-87).

The present inventors have identified optimal relative concentrations of fibrinogen, thrombin and platelet lysate for the compositions of the present inventions, some of which are described in the Examples and claims of the present application. It will be understood that the relative concentrations of fibrin, thrombin and platelet lysate disclosed are exemplary only.

Compositions according to the present invention may include cells. The cells may, for example, be mammalian cells (e.g. human cells, canine cells, feline cells, bovine cells, porcine cells, equine cells, caprine cells, hircine cells, murine cells, leporine cells, cricetine cells, musteline cells, or any combination thereof). The type of cells utilised will generally depend on the specific purpose for which the composition is to be used. For example, the cells may be of the same type as a tissue to which the composition is to be administered (e.g. eye surface cells including those of the central and/or peripheral corneal epithelium, bulbar and/or tarsal conjunctival epithelia, tarsal conjunctival stroma, and/or lid margin; skin cells including but not limited to keratinocytes, melanocytes, Merkel cells, and Langerhans cells; and neural tissue cells including but not limited to neurons and glial cells). Other examples include epithelial cells, keratocytes, neuronal cells, and endothelial cells. In some embodiments, the cells may be hematopoietic stem cells, bone marrow stem cells, neural stem cells, epithelial stem cells, skin stem cells, muscle stem cells, adipose stem cells, pluripotent stem cells, induced pluripotent stem cells, embryonic stem cells, mesenchymal stem cells, or any combination thereof. In some embodiments, the cells may be neuronal cells.

The platelet lysates and/or cells of the compositions may be autologous (i.e. self-derived to a given subject intended to receive the composition, or (i.e. donor-derived).

The compositions of the present invention may comprise essential and/or non-essential amino acids. Non-limiting examples of suitable essential amino acids include isoleucine, leucine, lysine, methionine, phenylalanine, threonine, tryptophan, valine, cysteine, tyrosine, histidine and arginine.

The compositions of the present invention may comprise additional components (e.g. agent/s) including, but not limited to fibronectin, anaesthetics, antibiotics, growth factors (e.g. human epidermal growth factor (hEGF), platelet derived growth factor, vascular endothelial growth factor, fibroblast growth factor, epithelial growth factor, transforming growth factor [including beta], and connective tissue growth factor), fibrin stabilizing factors (e.g. tissue factor XIII), matrix protein/s (e.g. collagen, laminin, integrin) and any combination thereof.

The compositions of the present invention may include other suitable ingredients including water and/or culture medium (e.g. DMEM, DMEM/F-12, MEM, CnT-PR). The culture medium may comprise, for example, any one or more of Glycine, L-Alanine, L-Arginine hydrochloride, L-Asparagine-H$_2$O, L-Aspartic acid, L-Cysteine hydrochloride-H$_2$O, L-Cystine 2HCl, L-Glutamic Acid, L-Glutamine, L-Histidine hydrochloride-H2O, L-Isoleucine, L-Leucine, L-Lysine hydrochloride, L-Methionine, L-Phenylalanine, L-Proline, L-Serine, L-Threonine, L-Tryptophan, L-Tyrosine disodium salt dihydrate, L-Valine, Vitamins, Biotin, Choline chloride, D-Calcium pantothenate, Folic Acid, Niacinamide Pyridoxine hydrochloride, Riboflavin, Thiamine hydrochloride, Vitamin B12, i-Inositol, Inorganic Salts, Calcium Chloride ($CaCl_2$)) (anhyd.), Cupric sulfate ($CuSO_4$-$5H_2O$), Ferric Nitrate ($Fe(NO_3)_3$"$9H_2O$), Ferric sulfate ($FeSO_4$-$7H_2O$), Magnesium Chloride (anhydrous), Magnesium Sulfate ($MgSO_4$) (anhyd.), Potassium Chloride (KCl), Sodium Bicarbonate ($NaHCO_3$), Sodium Chloride (NaCl), Sodium Phosphate dibasic ($Na_2HPO_4$) anhydrous, Sodium Phosphate monobasic ($NaH_2PO_4$—, Zinc sulfate ($ZnSO_4$-$7H_2O$), Other Components, D-Glucose (Dextrose), Hypoxanthine Na, Linoleic Acid, Lipoic Acid, Putrescine 2HCl, Sodium Pyruvate, Thymidine, or any combination thereof.

In some embodiments, the compositions do not comprise anticoagulants or are substantially free of anticoagulants which may be present at only trace amounts. Non limiting examples of these anticoagulants include heparin, Vitamin K Antagonists (e.g. Warfarin, Coumarins), Rivaroxaban, Edoxaban, Apixaban, Dabigatran, and the like.

Non-limiting properties of the compositions include one or more of the following:

Non-Newtonian shear-thinning fluid properties, whereby the viscosity of the composition may decrease as the shear-rate increases. In some embodiments, the viscosity of the compositions may be in the range of 0.01 and 1000 Pa·s at room temperature.

Optically clarity without impeding or without substantially impeding vision arising from transmittance of light, for example, over 90% in the visual colour range of 400-700 nm.

Suitability for printing (e.g. bioprinting/extrusion printing) with capacity to maintain or substantially maintain shape/structure following printing.

Suitability for printing while maintaining the viability of cells within the composition during the printing process.

Capacity to be provided in two- or three-dimensional structure with or without the inclusion of viable cells.

Capacity to sustain and/or promote the growth of cells (e.g. sustain and/or promote the expansion growth of primary human cells such as epithelial cells, keratocytes, neuronal cells, and endothelial cells).

Capacity to promote the formation of spheroid organoids.

Capacity for degradation by cells over time (e.g. 2-7 days).

Wound healing capacity (e.g. corneal ulcers) over time (e.g. 7 days).

Maintenance of cell viability over time (e.g. 7 days at 34° C.).

Capacity to adhere to various surfaces, including tissues, organs, membranes (e.g. mammalian and human tissues, organs, membranes).

Preparation of Wound Healing Compositions

Compositions of the present invention comprise platelet lysate (e.g. mammalian platelet lysate, human platelet lysate). The platelet lysate may be prepared by any suitable method (e.g. lysing by freeze/thawing; see, for example, Chou and Burnouf, ISBT Science Series, Vol 12, Issue 1, February 2017, pages 168-175).

Additionally, the present inventors have observed that the use of anticoagulants during platelet lysate preparation (e.g. when culturing) can have an impact on the capacity of platelet lysates to form compositions according to the present invention. Accordingly, in some embodiments of the present invention, the platelet lysates utilised are prepared without anticoagulants (e.g. heparin) at some or all stages of the preparation method.

In general, the compositions of the present invention may be prepared by combining a plurality of different preparations. In some embodiments, a preparation comprising thrombin may be maintained separately from a preparation comprising fibrinogen, and the two preparations combined prior to or during application of the composition.

For example, a first preparation comprising fibrinogen and platelet lysate can be mixed with a second preparation comprising thrombin to provide composition of the invention. Alternatively, a first preparation comprising fibrinogen can be mixed with a second preparation comprising thrombin and platelet lysate to provide composition of the invention. Additional components (e.g. ions, a source of ions, amino acids, cells, antibiotics, growth factors, fibrin stabilizing factors, anaesthetics and so on) can be incorporated into the composition in any suitable manner, at any suitable time (e.g. before the mixing stages). In some embodiments, some or all of the additional components (i.e. components additional to fibrinogen and thrombin) can be included in the preparation comprising thrombin and/or the preparation comprising fibrinogen. In other embodiments, some or all of the additional components (i.e. components additional to fibrinogen and thrombin) can be provided in one or more preparations that are separate to those preparations comprising thrombin or fibrinogen. In still other embodiments, some of the additional components (i.e. components additional to fibrinogen and thrombin) can be included in the preparation comprising thrombin and/or the preparation comprising fibrinogen, and some of the additional components (i.e. components additional to fibrinogen and thrombin) can be included in one or more preparations that are separate to those preparations comprising thrombin or fibrinogen.

In some embodiments, the compositions can be prepared by establishing individual flow streams of separated components. These streams can be maintained in a state of continual flow for a suitable time period and be oriented to mix with each other at a given point to thereby provide a further stream of mixed components that is deposited on the biological target. Alternatively, the streams may be oriented to mix with each other at or on a surface of the biological target to which the composition is applied.

In some embodiments, the invention provides devices and/or kits that facilitate the separation of different preparations needed to form the compositions of the invention until use. In general, the devices and kits may comprise at least two physically separated compartments, a first comprising a preparation of thrombin and a second comprising a preparation of fibrinogen. In some embodiments, either or both compartments may comprise additional components to be used in generating the composition (e.g. platelet lysate, ions, amino acids, cells, antibiotics, growth factors, fibrin stabilizing factors, anaesthetics and so on).

The devices and kits may further comprise a component providing a means to facilitate mixing of the two compartmentalised preparations such as, for example, by removal of barrier/s separating the first and second compartments, and/or by puncturing a seal or wall of either or both compartments. The skilled person will readily understand that various arrangements can be made for this purpose.

Additionally or alternatively, devices and kits may be configured in a manner that ensures mixing of the two compartmentalised preparations during or following release of the preparations from the device or kit.

In some embodiments, the devices and kits may comprise additional compartments comprising additional components to be used in generating the composition (e.g. platelet lysate, ions, amino acids, cells, antibiotics, growth factors, fibrin stabilizing factors, anaesthetics and so on). The device or kit may be configured in such a way to facilitate mixing of these additional components with each other and/or with the preparation/s of fibrinogen and/or thrombin during use of the device or kit.

The devices and kits may facilitate mixing of separated components prior to, during or immediately following discharge of the components from the device or kit. In some embodiments, the devices and kits may provide a means to establish individual flow streams of the separated components. These streams can be maintained in a state of continual flow during use of the device or kit and be oriented to mix with each other at a given point. The point of mixing may be within the device or kit, at the site at which the streams exit the device or kit, or external to the device or kit (e.g. at or prior to a surface of a biological target to which the composition is being applied). In some embodiments, the compositions are bioinks and the device is a three-dimensional (3D) printer (e.g. an extrusion printer).

Applications of the Compositions

The present inventors have developed a composition for the delivery of agent/s to target tissues and cells with characteristics making it highly suitable for bioprinting. In addition to their use in therapeutic applications in wound healing, the compositions of the present invention may be used in therapeutic applications where there is a need for delivery of agents (e.g. natural growth factors, drugs, nanoparticles, and/or cells,) and/or for the fixation of individual biological surfaces, and/or in tissue culture methods.

In some embodiments the compositions can act as wound sealants and/or as a fixative for biological structures. They may provide structural and/or nutritional support to a wound. Additionally or alternatively, the compositions may facilitate the growth of target cell type/s, including those which may be provided as a component of the compositions and/or cells present in the wound area.

While no limitation exists as to the type of tissue to which the compositions may be applied, the present inventors have demonstrated that the compositions are highly effective in the treatment of eye wounds.

For example, the compositions are demonstrated herein to be effective in treating corneal wounds. In these embodiments, the compositions may be used to promote the proliferation and/or migration of corneal epithelial cells. The compositions may, for example, support multidirectional growth and/or stratification of corneal epithelial cells, which may partially or completely biodegrade the composition once a cell monolayer is formed.

The present invention thus provides methods for treating wounds, and medicaments manufactured for the such treatment methods. The wounds may, for example, be located in or around eye tissue including tissue of the central and/or peripheral corneal epithelium, bulbar and/or tarsal conjunctival epithelia, tarsal conjunctival stroma, and/or lid margin).

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific Examples, which should not be construed as in any way limiting.

Example One: Preparation and Characterisation of Bioink Compositions

Materials and Methods (i) Preparation of Platelet Lysate

Pharmaceutical Human Platelet lysate is prepared by Australian Red Cross Blood Service via two methods:
1. Apheresis
   a. Platelets are obtained via apheresis.
   b. Platelets are stored for 5 days at 4 degrees Celsius.
   c. Platelet lysate concentration is high due to apheresis process, but contains
   d. Platelet lysate is prepared via multiple freeze thaw cycles, with centrifugation and debris removed via opti-press at each round and then stored at −80° C.
2. Pooled
   a. Blood bags are hung and red blood cells separated via in-line filtration
   b. Plasma is spun in the bag and then plasma is separated via opti-press to a 30% plasma/platelet concentration
   c. Platelet products left in the bag are pooled in a closed system via tube welders.
   d. Pooled-platelets are stored for 5 days at 4 degrees Celsius.
   e. Pooled-platelet units are pooled into a 2 litre batch (50-70 donations)
   f. Pooled platelet units are then centrifugated and supernatant removed to obtain a concentration of approximately $2 \times 10^{11}$ platelets.
   g. Pooled platelet units is prepared via multiple freeze thaw cycles, with centrifugation and debris removed via opti-press and then stored at −80° C.

Notes:
   All hPL prepared was stable for up to 12 months at −80° C.
   The pooled platelets were not fibrinogen reduced due to the low plasma concentration of below 30%.
   They were prepared in a closed system via final centrifugation and sterile filtration to remove pathogens.
   All platelets were gamma irradiated post collection before their storage phase, no pathogen inactivation technologies were used.
   Lysate received from the Red Cross blood bank was thawed overnight at 4° C. then placed in the water bath at 37° C. for 2 hours. Following this it was stored at 4° C. if used immediately, or −80° C. until required.

(ii) Bioink Preparation

Pharmaceutical compositions ("bioink compositions") comprising platelet lysate, thrombin and fibrinogen were manufactured. In some cases the bioink compositions included additional ingredients such as ions, (e.g. calcium), pharmaceutically acceptable essential amino acids (e.g. isoleucine, leucine, lysine, methionine, phenylalanine, threonine, tryptophan, valine, cysteine, tyrosine, histidine and/or arginine), fibronectin, human endothelial growth factor, tissue factor XIII, anaesthetics, antibiotics, other growth factors (including but not limited to platelet derived growth factor, vascular endothelial growth factor, fibroblast growth factor, epithelial growth factor, transforming growth factor (including beta), and/or connective tissue growth factor), and/or other ingredients/excipients (see Table 1).

TABLE 1

Composition of bioink

|  | Components | Minimum Concentration |
|---|---|---|
| Essential Components | Fibrinogen | 1-20 mg/mL |
|  | Thrombin | 1 U/mL-20 U/mL |
|  | Platelet Lysate | (1-40%) |
| Other Potential Components | Fibronectin | 1 ng-1 mg/mL |
|  | hEGF | 1-50 ng/mL |
|  | Growth factors/ supplements/other agents specific to a certain cell-type | Variable |
|  | Anaesthetics | Variable |
|  | Antibiotics | Variable |
|  | Ions e.g. calcium | Variable |
|  | Tissue Factor XIII | 1 ng-1 mg/mL |
|  | Amino acids | Variable |

The compositions were manufactured by first preparing two separate solutions A and B (see Table 2) which were mixed together prior to application of the bioink. The mixing does not need to be complete and partial mixing was sufficient to cause the bioink to form.

TABLE 2

Mixing of the two solutions to form bioink

|  | Solution A | Solution B |
|---|---|---|
| Active Ingredients | Human Platelet Lysate Fibrinogen | Thrombin (human) Calcium chloride |
| Excipients | Amino acids Ions Antibiotics Anaesthetics Water for Injection | Ions Water for Injection |

Results and Discussion

The bioink was produced upon mixing of solutions A and B forming a transparent and colourless gel. The following properties of the bioink were noted.

The bioink is a non-Newtonian shear-thinning fluid, whereby its viscosity decreases as the shear-rate increases. The viscosity of the bioink is in the range of 0.01 and 1000 Pa·s at room temperature.

The bioink is optically clear and does not impede vision due to a transmittance of light over 90% in the visual colour range of 400-700 nm.

The bioink can maintain its printability via extrusion printing and hold its shape once extruded, as determined by rheology.

The bioink can adhere to the tissues

The bioink can sustain and promote the growth of cells in tissue culture without secondary support media.

The bioink can sustain and promote the expansion growth of primary human cells such as epithelial cells, keratocytes, neuronal cells, and endothelial cells.

The bioink promotes the formation of spheroid organoids.

Cells can degrade the bioink over a period of 2 to 7 days and resorb the bioink matrices.

The bioink can heal wounds such as corneal ulcers over the course of 7 days.

The bioink maintains the viability of cells within the bioink for up to 7 days when stored at 34° C.

The bioink allows 3D cell printing by suspending cells in the first component

The bioink provides both structural support (scaffold) and nutritional support concurrently that encourages cell growth and healing.

The bioink facilitates the growth of multiple cell types

The bioink is able to promote the growth of multiple cell types in the cornea allowing it to act as a wound healing treatment that extends through multiple layers of the cornea and/or to encourage neuronal outgrowths from human corneal explants. SHSY5Y, a neuronal cell line that is not of corneal origin was successfully cultured in the bioink allowing for applications that span beyond the cornea.

The bioink is able to be used in tissue culture to create spheroid aggregates of cells. The aggregates can be made simpler fashion as compared to known methods, and generate spheroids without the need to digest the tissue via enzymes or use microwells.

The bioink is versatile and customizable and can be tailored to individual patients' needs encompassing a wider range of applications that can extend across more pathologies and also more tissue types. Autologous platelet lysate or lysate from a donor can be included in the bioink depending on what is most advantageous to the patient. Antibiotic and anaesthetic/analgesic concentrations and type can be customized to target specific infections/maladies and cater for potential patient allergies. Preliminary data of using components such as collagen and other proteins in the bioink as well as different concentrations of various factors has allowed modification and optimisation of its mechanical and nutritional profile for various applications.

The bioink can be used to fill in ocular defects at a high resolution, is liquid and sets in a matter of minutes once mixed and at the wound-site independent to temperature. The bioink is capable of filling defects efficiently and retaining shape to potentially accelerate wound healing and/or reduce the amount of time required in the clinic. The shear-thinning properties of the bioink can be provided in a range that makes it compatible with extrusion and droplet based bio-printing.

The bioink is substantially transparent a feature that is advantageous for retaining vision in addition to promoting wound healing and cell growth in the cornea.

The bioink can thus provide both structural and nutritional support to, for example, corneal cells, has a wide range of potential applications, has favourable physical properties and has been shown to generate neuronal outgrowths and spheroid aggregates in primary culture.

Example Two: Optimisation of Bioink Formulations and Exemplary Characteristics

Materials and Methods (i) Reagents and Antibiotics

Dulbecco's modified Eagle's medium/F12 GlutaMax™ without phenol red (DMEM/F12), phosphate-buffered saline (PBS), TrypLE, penicillin/streptomycin, were purchased from Gibco. Human platelet lysate was obtained from Red Cross Blood Bank. Foetal bovine serum (FBS) was purchased from Corning (USA). Human epidermal growth factor (hEGF), penicillin-streptomycin [(P-S), 10,000 U/mL] were purchased from Life technology (USA).

Fibrinogen and thrombin were purchased from Merck Millipore. Haematoxylin & eosin were purchased from Sigma-Aldrich (USA).

(ii) Sample Recruitment

Human corneas unsuitable for grafting were provided by the Lions NSW Eye Bank with consent and ethics approval from the Local Health District Human Research Ethics Committee (HERC 14/275). All procedures were in accordance with the Declaration of Helsinki.

Frozen porcine eyes were obtained from Sight Foundation Training Laboratory. Sydney Eye Hospital.

(iii) Scratch Assay

SV40-immortalized human corneal epithelial cell line (HEC-T, Rilka, Japan) was thawed and cultured in the 5% FBS medium (5% FBS, 10 ng/ml hEGF, 5% P-S, DMEM/F12 glutmax) until 80% confluent. The cells were then passaged into two T-75 flasks, with one cultured with the 5% FBS medium, and the other were grown in 5% hPL medium (5% hPL, 10 ng/ml hEGF, 5% P-S, DMEM/F12) until 80% confluent. HCE-T cells from 5% FBS were then seeded in a 24 well plate (20,000 cells/well) in six wells and left until fully confluent. Similarly, HCE-T cells from 5% hPL were seeded in the same 24 well plate in three wells at the same density and left until fully confluent. Medium was changed every 2 days. Three out of the 6 wells cultured in 5% FBS were replaced with DMEM one day before scratching. After scratching, all wells were monitored and image captured every 2 hours using an Olympus DP70 light microscope (Olympus, USA) with 4× objectives. All images were analysed by Image J (v1.51). The rate of wound closure was calculated as the decrease in wound size over 5 hours for the first 5 hours. This was calculated in Excel (Microsoft) and graphed and statistically analysed in Prism (GraphPad, USA).

(iv) Bioink Formulation Testing

Bioink Preparation

The hPL received was thawed overnight at 4° C., followed by incubation in a water bath at 37° C. for 2 hours. The hPL were then stored at 4° C. until further use.

Fibrinogen was dissolved in sterile water at 37° C. and aliquoted into 1 mL Eppendorf tubes at a concentration of 20 mg/mL. These were stored at −20° C. and thawed at 37° C. immediately before use.

Thrombin was dissolved in DMEM/F12 and aliquoted into 1 mL Eppendorf tubes at a concentration of 20 U/mL. These were stored at −20° C. and thawed at 37° C. immediately before use.

The bioinks were made up by equal mixing of two separate components: component one contains hPL and fibrinogen in DMEM/F12; and component two contains thrombin in DMEM/F12. Various concentrations of fibrinogen (0.2, 2 and 5 mg/mL) and thrombin (1, 5, 10 units/mL) were tested. All bioinks contained an initial concentration of 20% hPL (Table 1).

TABLE 3

Nine bioink formulations tested with their separate component compositions listed. All the concentrations tested refer to pre-mixing concentrations.

| Bioink 1 | | Bioink 2 | | Bioink 3 | |
|---|---|---|---|---|---|
| 20% hPL | 2 U/mL | 20% hPL | 2 U/mL | 20% hPL | 2 U/mL |
| 0.4 mg/mL | Thrombin | 4 mg/mL | Thrombin | 10 mg/mL | Thrombin |
| Fibrinogen | DMEM/ | Fibrinogen | DMEM/ | Fibrinogen | DMEM/ |
| DMEM/ | F12 | DMEM/ | F12 | DMEM/ | F12 |
| F12 | | F12 | | F12 | |

TABLE 3-continued

Nine bioink formulations tested with their separate component compositions listed. All the concentrations tested refer to pre-mixing concentrations.

| Bioink 4 | | Bioink 5 | | Bioink 6 | |
|---|---|---|---|---|---|
| 20% hPL | 10 U/mL | 20% hPL | 10 U/mL | 20% hPL | 10 U/mL |
| 0.4 mg/mL | Thrombin | 4 mg/mL | Thrombin | 10 mg/mL | Thrombin |
| Fibrinogen | DMEM/ | Fibrinogen | DMEM/ | Fibrinogen | DMEM/ |
| DMEM/ | F12 | DMEM/ | F12 | DMEM/ | F12 |
| F12 | | F12 | | F12 | |

| Bioink 7 | | Bioink 8 | | Bioink 9 | |
|---|---|---|---|---|---|
| 20% hPL | 20 U/mL | 20% hPL | 20 U/mL | 20% hPL | 20 U/mL |
| 0.4 mg/mL | Thrombin | 4 mg/mL | Thrombin | 10 mg/mL | Thrombin |
| Fibrinogen | DMEM/ | Fibrinogen | DMEM/ | Fibrinogen | DMEM/ |
| DMEM/ | F12 | DMEM/ | F12 | DMEM/ | F12 |
| F12 | | F12 | | F12 | |

Rheology

The rheological properties of the prepared inks were examined by an AR-G2 rheometer (TA Instruments, USA). A 2°/40 mm cone plate geometry was used in all tests. A time sweep test was conducted to determine the consistency of the ink at a constant frequency of 1 HZ and strain at 1%. The temperature was also kept constant at 34° C. to mimic the temperature at the corneal surface. The Storage modulus (G') and loss modulus (G") of each bioink (n=3 per bioink) as a function of time over 10 minutes was measured. The data was tabulated, graphed and analysed using Prism (GraphPad, USA).

Shear thinning is an ideal property for extrusion-based bioprinting, as a result, the ink viscosity in response to applied shear stress was also measured by the rheometer. The viscosity across a shear rate ramp between $0.1\ s^{-1}$ and $100\ s^{-1}$ was measured at a fixed temperature of 34° C. for each bioink (n=3 per bioink) was measured. The data was tabulated, graphed and analysed using Prism (GraphPad, USA).

Transparency

Mean transmittance of light was measured across the visible spectrum (400-700 nm). The machine was zeroed for a glass slide and samples were subsequently placed on the slide (n=3 per sample) and mean transmittance was measured. A visual representation of the ink's transparency was created by writing "Cornea" with the ink on glass slide and held in the light.

Cell Compatibility

Bioinks prepared as described above were also used for cell compatibility tests. HCE-T cells (passage number 23) were seeded in a 96 well plate (6000 cells/well, n=6 per condition) and confluence was measured every 2 hours over 7 days using Incucyte™ (ZOOM, Essen BioScience Inc).

All subsequent experiments were performed using one formulation of bioink 5 (Table 3, premixing concentration: 20% hPL, 4 mg/mL fibrinogen, 10 U/mL thrombin, DEME/F12).

Culturing Corneal Explants

Corneal explants were obtained from the Lions NSW Eyebank. The limbal and central region were separated using an 8 mm trephine. The limbal region was then dissected into 8 equal sized pieces with as much sclera as possible removed and placed in one well of a 6 well plate and the central region was dissected into 8 equal sized pieces and placed into another well of the 6 well plate. The explanted pieces were then covered with 2 mL of bioink 5 (Table 3).

(v) Ex Vivo Wound Healing Test

The epithelium of an ulcerated cornea (received from the Lions NSW Eye Bank) was removed by surgical spade and rinsed with PBS. Bioink 5 (Table 3) was immediately applied on the wound surface. The cornea was then suspended in a jar of organ culture media. The ink was reapplied at day 4. At day 7, the cornea was fixed overnight with 4% paraformaldehyde, rinsed with PBS how many twice and left in 30% sucrose overnight. The cornea was then cut in half, immersed in OCT compound (Tissue-Tek, USA), snap-frozen in liquid nitrogen and stored at −80° C. until sectioning. Frozen corneas were sectioned to a thickness of 12 μm at −20° C. using a Leica CM3050 S cryostat (Leica Biosystems, Germany), and were transferred onto polylysine coated slides, dried and stored at −20° C. For Mayer's haematoxylin and eosin staining, the slides were dipped in 95% ethanol for 15 seconds, then dipped in 4% paraformaldehyde for 10 dips. The slides were then rinsed in distilled water for 10 dips and suspended in the Haematoxylin for 30 seconds. The slides were then dipped 10 times in two changes of distilled water each, followed by a further 10 dips in 95% ethanol. The slides were then counterstained in Eosin for 15 seconds, then dehydrated in 2× changes of 95% ethanol and 2 changes of 100% ethanol with 10 dips in each. The slides were then dipped 10 times each in 2 changes of xylene and mounted in DPX (Sigma-Aldrich). Sections were examined with an Olympus DP70 light microscope. A human donor cornea was used as a negative control, with its epithelium removed and immediately fixed, sectioned and stained using the same protocol.

(vi) Ex Vivo Perforation Test

Corneas from frozen porcine eyes (n=3) were excised and then secured in Barron artificial anterior chambers. The corneas were inflated by injecting water though syringes connected to the artificial anterior chambers. A metal skewer (1 cm diameter) was used to create a perforation in each cornea, and water leakage was observed to confirm a full thickness perforation had been created. The bioink 5 (Table 3) was then applied at the perforated site and left to set for 2 minutes. The corneas was then reinflated and any subsequent water leakage was observed.

(vii) Culturing a Cell Line of Non-Corneal Origin

SHSY-5Y cells were thawed and cultured in the bioink 5 (Table 3) in a T-25 flask. Cell morphology and confluence was observed by Olympus DP70. Cells were passaged when they reached 80% confluence, and the number of passage was recorded.

Creating the Bioink with Calcium Ion Solution and MEM to Replace the DMEM/F12 Component of the Bioink A calcium chloride solution (concentration of 200 mg/mL) and MEM were used to replace the DMEM//F12 component of the bioink and the final product was observed for gelation.

(viii) Statistical Analysis

All statistical analysis was performed in Prism (GraphPad, USA). T-tests were used to compare two individual conditions. Where three or more formulations were used, one—

Results and Discussion (i) Scratch Assay

Wells treated with 5% hPL and 5% FBS were completed healed at 24 hours with what rate and what rate respectively (FIG. 1). No significant difference (p>0.05) was observed. Wound closure was not observed in the DMEM only condition after 24 hours.

(ii) Rheology

The time sweep experiments showed that bioink formulations 2-9 (Table 3) are capable of gelation as the storage modulus was greater than the loss modulus (FIG. 2) and the ink was consistent as both moduli were stable over time (FIG. 2). Measuring viscosity over time demonstrated that all bioink formulations 1-9 (Table 3) exhibited non-Newtonian fluidic and shear-thinning behaviour as the viscosity decreased for all bioinks as the shear rate increased (FIG. 3).

(iii) Transparency

All variations of the ink (Table 3) displayed above 85% transparency for wavelengths in the visible spectrum (FIG. 4). Direct assessment of the ink transparency reinforced the printability of the ink as it can be extruded and retained shapes and the transparency as the buildings can be easily seen through the ink (FIG. 5).

(iv) Cell Compatibility

Except bioink formulations 6 and 9 (Table 3), cells confluence increased over time, suggesting the bioink formulations 1-5 and 7-8 support cell growth (FIG. 6). Cells cultured in ink with pre-mixed thrombin concentrations of 20 U/mL with 4 and 10 mg/mL of fibrinogen showed no increase in mean confluence. In addition, mean confluence rate also decreased as fibrinogen concentration increased. Corneal epithelial cells, keratocytes, endothelial cells and neuronal cells were observed to be growing in the bioink (FIG. 7). bioink degradation was also observed once the cells began to migrate out of the explants (FIG. 7a).

(v) Ex Vivo Wound Healing

Multiple cellular layers were observed in the ulcerated cornea treated with the bioink compared to de-epithelialiased cornea (FIG. 8). This demonstrated that the bioink is able to facilitate complete re-epithelialisation of an ex vivo ulcerated human cornea.

(vi) Perforation Test

All three perforated corneas demonstrated complete wound-sealing with the ink application with a 2 min setting time (FIG. 9).

(vii) Compatibility with Other Cell Types

SH-SY cells were able to reach confluency and were successfully cultured over 8 passages (FIG. 10) tested with bioink from Table 3.

Discussion

A transparent, printable, biocompatible and biodegradable platelet lysate based ink was developed for wound healing on the ocular surface. 5% hPL facilitated scratch healing in corneal epithelial cell lines at a comparable rate to foetal bovine serum (FBS), which is what is currently being used in standard tissue culture protocols. Through the addition of fibrinogen and thrombin to platelet lysate, it was possible to induce a 3D fibrin matrix formation and manipulate properties such as biocompatibility, strength and printability.

To the best of the inventors' knowledge Human platelet lysate has not been used as a standalone bioprinting material. This is because platelet lysate alone is not a strong enough matrix to be printed on its own. The ability for platelet lysate to form a gel depends on its preparation method. For tissue culturing, heparin is generally added to the platelet lysate to prevent clot formation. Clotting time, centrifugation and dilution of the blood products used have varied across studies, however these parameters have been shown to affect the efficacy and properties of blood products in general.

Through the development of two separate chambers (the first containing 20% hPL, 4 mg/mL fibrinogen, DMEM/F12 and mixing the two ingredients from the two chambers was able to generate a transparent, adhesive and bioprintable ink, which set as a 3D matrix directly at the wound site was achieved. The time sweep rheology experiment (FIG. 2) demonstrated the minimal requirements for the ink to be printable consists of fibrinogen≥ 0.2 mg/ml, thrombin>1 unit/mL and hPL at 10% (all concentration refer to pre-mixing stage). The hPL needs to be prepared as described in the method section to retain its bioactivity and heparin needs to be avoided in hPL preparation as it prevents the fibrin mesh formation. All ink compositions showed high transparency across wavelengths in the visible spectrum making this product ideal for an ophthalmic application (FIGS. 4 and 5). The cell compatibility tests demonstrated that the ink cannot have thrombin≥10 U/mL (FIG. 6) in order for effective cell confluency to result.

Through the combination of the cell compatibility and the rheological data an advantageous pre-mixed concentrations of fibrinogen and thrombin in the ink were observed to be 4 mg/mL and 10 U/mL respectively (bioink 5 in Table 3). Those concentrations were used in subsequent ex vivo studies which demonstrated that the bioink has the ability to facilitate complete re-epithelialisation of an ulcerated human cornea (FIG. 8) and to seal a complete perforation of 1 cm in diameter (FIG. 12). In addition, all four cell types were shown to be able to be grown in the bioink (FIG. 7), allowing this product has to serve as a full thickness, intraocular application. All these results show that the bioink has characteristics for treating corneal wound healing in a 3D printing fashion.

The concept of using 3D printing in the cornea is mainly associated with bioprinting the entire or partial structure externally, however the ability to print in vivo is advantageous to treat corneal wounds which have various sizes and require prompt attention. Fibrin glue, which is used commercially to seal wounds, is opaque, has been shown to only act to seal wounds and does not promote corneal cell growth as it inhibits corneal cell migration. This impedes the natural wound healing response and thus overall wound healing. The bioink generated incorporates the structural support fibrin glue can provide with the added benefits of allowing cell migration and proliferation, and can also include supplements that enhance corneal regeneration.

In additional to its printability, the bioink provides both structural and nutritional support concurrently that encourages cell growth and healing. Furthermore, the nature of bioink product is versatile and customizable and can be tailored to individual patients' needs with potential to cover a wide range of applications extending across more pathologies and more tissue types. Autologous platelet lysate or lysate from a donor can be included in the bioinks depending what is most advantageous to the patient. Antibiotic and anaesthetic/analgesic concentration and type can be customised to target specific infections/maladies and cater for potential patient allergies. The bioink may also be used as drug delivery tool to extend the half-life and accurately deliver the drugs directly to the wound site. It can also be used to delivery other substances such as nanoparticles to targeted sites.

The formation of spheroid cells is an indication of 3D culturing (FIG. 11). In the last decade, there has been heightened interest in developing 3-dimensional cell aggregates for corneal applications. 3-dimensional cell aggregates have been shown to facilitate tissue self-assembly at a greater rate than 2-dimensional monolayer cell cultures. This method of cell culturing is particularly advantageous as compared to single celled primary cultures, not only because this configuration facilitates more intercellular adhesions, but also because it can revert cells into a younger progeny whereby these cells possess stronger progenitor potential, migrate and proliferate at a greater speed than their primary culture equivalent, and possess heightened telomerase activity and telomere length. This method of cell culturing shows immense promise for corneal wound healing applications. The bioink can be used to an alternative matrix in 3D culturing and represents a simpler means of obtaining spheroidal cells.

Finally, the tissue culture results demonstrated that the bioink has the ability to support SHSY-5Y (a non-corneal derived neuronal cell line) (FIG. 10) indicating a range of potential future applications for this ink that extend broader than the cornea.

In conclusion, we the present inventors developed a bioink that is bioprintable, bio-degradable, transparent and having properties to facilitate wound healing. The bioink is also envisaged to possess additional functions such as a tool for 3D culturing to generate spheroid cells, ability to heal wounds in other tissues and act as an effective drug/substance carrier to disease treatments.

Example Three: Three-Dimensional Printing of Bioink Formulations in Layers

Methods

P18 HCET cells were trypsinised and suspended in the bioink at a final concentration of 1×10$^6$ cells/mL. The bioink was then extruded in a petri dish and left to set for 2 minutes. Another layer of ink was then extruded on top orthogonally and left to set. The two lines were observed under a light microscope to determine if they remain distinct.

Results

As demonstrated in FIG. 13, the bioink is printable in distinct layers.

Example Four: Survival of Cells in Printed Bioink

Methods

P18 HCET cells were trypsinised and suspended in the bioink at a final concentration of 1×10$^6$ cells/mL. The bioink was then extruded in a petri dish and left to set for 2 minutes. Hoescht and propidium iodide (PI) live-dead staining was performed at 2 and 72 hours post extrusion and cell viability was calculated with image J. Hoescht staining (blue) stains for all cell nucleus, whereas PI staining (red) only stains for dead cells.

Results

FIGS. 14A and 14B show Hoescht and propidium iodide staining in the same region at 2 hrs post extrusion. FIGS. 14C and 14D show Hoescht and propidium iodide staining in the same region at 72 hrs post extrusion.

Image J analysis determined cell viability to be over 90% in both cases meaning that the product can be used as a cell carrier to 3D print cells.

Example Five: Role of Calcium Ions in Formation of Bioink

Methods

The conditions were tested as shown in Table 3 (n=3 per condition)

TABLE 4

Conditions utilised

| 20% hPL 4 mg/mL fibrinogen 10 U/mL thrombin DMEM (calcium ion containing solution) | 20% hPL 4 mg/mL fibrinogen 10 U/mL thrombin PBS (calcium free ion solution) | 20% hPL 4 mg/mL fibrinogen 10 U/mL thrombin water | No hPL 4 mg/mL fibrinogen 10 U/mL thrombin DMEM (calcium ion containing solution) | No hPL 4 mg/mL fibrinogen 10 U/mL thrombin DMEM (calcium free ion solution) | No hPL 4 mg/mL fibrinogen 10 U/mL thrombin DMEM water |
|---|---|---|---|---|---|

Results

A transparent gel was achieved in all solutions containing hPL independent of calcium ions. An opaque gel was achieved in the condition where no hPL was used but calcium ions were present. No hPL and no calcium ions resulted in fibrin pieces floating on top of a clear liquid and no gel formation.

hPL is essential for gelation and transparency of the ink (FIG. 15). The bioink was able to form independently of the calcium ions.

Example Six: Addition of Components to Bioink

Methods

Different components were added to the bioink at various concentrations (Table 5) (n=3 per formulation) and extruded as 3 drops on a glass slide. The first drop was allowed to set for 1 min, the second 2 mins and the third 5 mins. At these time points they were then subject to the 'dipping test' whereby they were dipped in water and then rinsed with 0.9% NaCl. Minimum setting time was determined by the shortest timepoint at which the gelated drop remained on the slide post 'dipping test'.

TABLE 5

Various concentrations of different components tested

| 1 | 2 | 3 | 4 |
|---|---|---|---|
| 10% (v/v) hPL 2 mg/mL Fibrinogen 5 U/mL Thrombin | 10% (v/v) hPL 2 mg/mL Fibrinogen 5 U/mL Thrombin 10 µg/mL Factor Xiii | 10% (v/v) hPL 2 mg/mL Fibrinogen 5 U/mL Thrombin 1 µg/mL Factor Xiii | 10% (v/v) 2 mg/mL Fibrinogen 5 U/mL Thrombin CnT-PR (epithelial specific media) |

| 5 | 6 | 7 |
|---|---|---|
| 10% (v/v) hPL 2 mg/mL Fibrinogen | 10% (v/v) hPL 2 mg/mL Fibrinogen | 10% (v/v) hPL) 2 mg/mL Fibrinogen |

TABLE 5-continued

Various concentrations of different components tested

| 5 U/mL Thrombin Endothelial specific media | 5 U/mL Thrombin 3 mg/mL type 1 collagen(calf skin) | 5 U/mL Thrombin 0.5 mg/mL fibronectin |
|---|---|---|

Results

All compositions were able to set at or under 5 minutes post mixing (Table 6). FIG. 16 shows images of the bioink on the glass slides post dipping tests. A. shows composition 1, B. shows composition 2, C. shows composition 3, D. shows composition 4, E. shows composition 5, F. shows composition 6, E. shows composition 7 as per Table 5.

TABLE 6

Minimum setting time for the different compositions

| Composition | Setting time |
|---|---|
| 1 (bioink only) | 2 mins |
| 2 (10 µg/mL FXiii) | 1 min |
| 3 (1 µg/mL FXiii) | 1 min |
| 4 (CnT-PR) | 5 mins |
| 5 (Endothelial specific media) | 5 mins |
| 6 (3 mg/mL collagen) | 5 mins |
| 7 (0.5 mg/mL fibronectin) | 2 mins |

Example Seven: Use of the Bioink as an Ocular Surface Sealant

Methods

Experiments in this Example were performed using one formulation of bioink 5 (Table 3), premixing concentration: 20% hPL, 4 mg/mL fibrinogen, 10 U/mL thrombin, DEME/F12). A wound of approximately 1.5 mm in diameter was created centrally in human corneas obtained from the Lions NSW Tissue Bank. The corneas were then placed in a Hanna artificial anterior chamber (AAC). Bioink (n=3) was administered on the wounds and subjected to increasing pressures. The pressure at which perforated corneas with no sealant exhibited stable leaking was measured and taken as the baseline pressure inherent in the system. Failure of the sealant was determined to be when the wound was observed to leak and the burst pressure was calculated as:

peak force experienced before leakage−baseline force/surface area of the anterior chamber and recorded in mmHg.

Results

The results (see FIGS. 17 and 18) demonstrate that bioink can be used as a sealant for small corneal perforations and as a biocompatible alternative to commercially available sealants such as cyanoacrylate glue. In perforations of roughly 1.5 mm in diameter, the bioink was able to withstand a mean pressure of 91±27 mmHg. This well exceeds mean intraocular pressure (10-22 mmHg).

Example Eight: Setting Time Versus Fixed Shear Rate

Methods

Experiments in this Example were performed using one formulation of bioink 5 (Table 3), premixing concentration: 20% hPL, 4 mg/mL fibrinogen, 10 U/mL thrombin, DEME/F12). The setting time of the bioink was quantitatively measured at a fixed shear rate of 1 s$^{-1}$. A couette cup and bob viscometer geometry was also used in the AR-G2 rheometer (TA Instruments, USA) to determine viscosity at a fixed shear rate of 1 s$^{-1}$ of the bioink (n=3). 15 mL of component A (20% hPL, 4 mg/mL hPL, DMEM/F12) was poured into the geometry and viscosity was measured for component A alone for 60 seconds. The bob then paused rotation for 5 seconds during which 15 mL of component B (10 U/mL thrombin, DMEM/F12) was added. The bob then recommenced rotating and viscosity was measured for a further 180 seconds. The data was tabulated, graphed and analysed using Prism (GraphPad, USA). The setting time was established and determined to be the time taken to reach a stable viscosity after the addition of Component B.

Results

The bioink set in 25 seconds (FIG. 19) when mixed at a fixed shear rate of 1 s$^{-1}$. It had previously been determined to set in 2-5 minutes when components A and B are mixed passively on the benchtop. These results demonstrate that shear rate affects setting time, meaning that the resolution at which the bioink is extruded at in a 3D printing device affects how rapidly the bioink sets.

Example Nine: In Vivo Animal Trials

Methods

Experiments in this Example were performed using one formulation of bioink 5 (Table 3), premixing concentration: 20% hPL, 4 mg/mL fibrinogen, 10 U/mL thrombin, DEME/F12).

Experiments were performed to determine whether the bioink facilitates/does not hinder wound healing in an in vivo corneal epithelial wound model and an in vivo corneal perforation model, and to ascertain whether it reduces pain experienced associated with the wound healing process.
Subjects: Female New Zealand Albino White Rabbits
Epithelial Wound (Rabbits 1 and 2)
1. The rabbit subjects will be prepared for the procedure using the SOP Anaesthesia and Analgesia Rabbits (Hybrid Theatre) Procedures (SOP-ANA_04_LAS anaesthesia and analgesia_rabbits_20171130) and LAS SOP #38 Handling and Restraint of Rabbits.
2. Buprenorphine patch is placed on the rabbits back prior to the procedure.
3. The eyelid margin is prepared by removing the fur from the periocular region. This is completed by the veterinarian assistant using veterinarian clippers (#40 blade).
4. The ocular surface and periocular skin surface region is prepped with 10% povidone-iodine wash.
5. The sterile surgical drape is placed over the rabbit exposing the periocular region.
6. The paediatric speculum is placed in the eye to maintain access during the procedure.
7. The cornea is then flushed with sterile saline to remove the 10% povidone-iodine wash.
8. Surface is dried by applying the surgical spears lightly to the cornea.
9. A 5 mm sterile corneal light shield (sponge) is prepared with 3 drops (approx. 150 microlitres) of 30% ethanol. The sponge is then placed on the central corneal surface for 20 seconds to facilitate the loosening of the epithelial cells from the underlying corneal layers. Care is taken to observe the sponge for the possibility of residual liquid leaking from the sponge. This can be ameliorated by the use of a surgical spear to absorb the additional fluid (if required).
10. Surgical forceps are then used to remove the corneal light shield/sponge which is then discarded. A surgical spear is then used to absorb residual ethanol liquid on the cornea.
11. The loosened epithelium is removed by bringing the surgical spear across the central 5 mm area. If the epithelium cannot be removed by the use of a surgical spear, the investigator will use the sterile hockey blade to gently remove the remaining cells.
12. If the rabbit is considered a study rabbit, the bioink will be placed over the central 5 mm defect. A timer is started for 120 seconds to ensure adequate adhesion to the exposed corneal surface.
13. Antibiotic eye drops are placed in the operated eye and the speculum is removed. The rabbit is provided Meloxicam 0.5 mg/kg. Meloxicam is administered by the veterinarian anaesthetist.
14. The investigator externally examines the wound and surrounding area to confirm the absence of intraoperative complications.
15. Once the procedure is completed the rabbit is moved to recovery for monitoring. Prior to return to the individual housing a drop of Celluvisc artificial tears is placed in both eyes. Celluvisc is placed in the operated eye prior to antibiotic eye drops and up to every 2 waking hours until wound closure. Refresh preservative free gel lubricants will be placed in the operated eye at the final examination of the day to provide extended coverage overnight. This will continue until wound closure also or, if in the opinion of the investigators, the rabbit subject is exhibiting surface irritation under slit lamp examination (e.g. chemosis, dry or irregular corneal surface).
16. Pain is scored every 2 hours throughout working hours as per the HT composite pain score rabbits document.
17. General examination will occur 4 times per day until wound is healed as indicated by slit lamp biomicroscopy (up to 7 days), then followed by once a day for the 7 days post wound closure followed by once every weekday until euthanasia.
Corneal Perforation (Rabbits 3, 4 and 5)
1. The rabbit subjects will be prepared for the procedure using the SOP Anaesthesia and Analgesia Rabbits (Hybrid Theatre) Procedures (SOP-ANA_04_LAS anaesthesia and analgesia_rabbits_20171130) and LAS SOP #38 Handling and Restraint of Rabbits.
2. Buprenorphine patch is placed on the rabbits back prior to the procedure.
3. The eyelid margin is prepared by removing the fur from the periocular region. This is completed by the veterinarian assistant using veterinarian clippers (#40 blade).
4. The ocular surface and periocular skin surface region is prepped with 10% povidone-iodine wash.
5. The sterile surgical drape is placed over the rabbit exposing the periocular region.

6. The paediatric speculum is placed in the eye to maintain access during the procedure.
7. The cornea is then flushed with sterile saline to remove the 10% povidone-iodine wash.
8. Surface is dried by applying the surgical spears lightly to the cornea.
9. A blade is used to create a complete perforation of approximately 2 mm in length in the peripheral region of the cornea.
10. If the rabbit is considered a study rabbit, the BioInk will be placed over the perforation. A timer is started for 120 seconds to ensure adequate adhesion to the exposed corneal surface.
11. If the rabbit is considered a control rabbit, commercially available histoacryl will be placed over the perforation.
12. Antibiotic eye drops are placed in the operated eye and the speculum is removed. The rabbit is provided Meloxicam 0.5 mg/kg. Meloxicam is administered by the veterinarian anesthetist.
13. The investigator externally examines the wound and surrounding area to confirm the absence of intraoperative complications.
14. Once the procedure is completed the rabbit is moved to recovery for monitoring. Prior to return to the individual housing a drop of Celluvisc artificial tears is placed in both eyes. Celluvisc is placed in the operated eye prior to antibiotic eye drops and up to every 2 waking hours until wound closure. Refresh preservative free gel lubricants will be placed in the operated eye at the final examination of the day to provide extended coverage overnight. This will continue until wound closure also or, if in the opinion of the investigators, the rabbit subject is exhibiting surface irritation under slit lamp examination (e.g. chemosis, dry or irregular corneal surface).
15. Pain is scored every 2 hours throughout working hours as per the HT composite pain score rabbits document.
16. General examination will occur 4 times per day until wound is healed as indicated by slit lamp biomicroscopy (up to 7 days), then followed by once a day for the 7 days post wound closure followed by once every weekday until euthanasia.

Modified Corneal Perforation (Rabbits 6 and 7)
1. The rabbit subjects will be prepared for the procedure using the SOP Anaesthesia and Analgesia Rabbits (Hybrid Theatre) Procedures (SOP-ANA_04_LAS anaesthesia and analgesia_rabbits_20171130) and LAS SOP #38 Handling and Restraint of Rabbits.
2. Buprenorphine patch is placed on the rabbits back prior to the procedure.
3. The eyelid margin is prepared by removing the fur from the periocular region. This is completed by the veterinarian assistant using veterinarian clippers (#40 blade).
4. The ocular surface and periocular skin surface region is prepped with 0.2% povidone-iodine wash.
5. The sterile surgical drape is placed over the rabbit exposing the periocular region.
6. The paediatric speculum is placed in the eye to maintain access during the procedure.
7. The cornea is then flushed with sterile saline to remove the 0.2% povidone-iodine wash.
8. Surface is dried by applying the surgical spears lightly to the cornea.
9. A blade is used to create a complete perforation of approximately 2 mm in length in the peripheral region of the cornea.
10. If the rabbit is considered a study rabbit, the BioInk will be placed over the perforation. A timer is started for 120 seconds to ensure adequate adhesion to the exposed corneal surface.
11. If the rabbit is considered a control rabbit, commercially available histoacryl will be placed over the perforation.
12. Antibiotic eye drops are placed in the operated eye and the speculum is removed. The rabbit is provided Meloxicam 0.5 mg/kg. Meloxicam is administered by the veterinarian anesthetist.
13. The investigator externally examines the wound and surrounding area to confirm the absence of intraoperative complications.
14. Once the procedure is completed the rabbit is moved to recovery for monitoring. Prior to return to the individual housing a drop of Celluvisc artificial tears is placed in both eyes. Celluvisc is placed in the operated eye prior to antibiotic eye drops and up to every 2 waking hours until wound closure. Refresh preservative free gel lubricants will be placed in the operated eye at the final examination of the day to provide extended coverage overnight. This will continue until wound closure also or, if in the opinion of the investigators, the rabbit subject is exhibiting surface irritation under slit lamp examination (e.g. chemosis, dry or irregular corneal surface).
15. Pain is scored every 2 hours throughout working hours as per the HT composite pain score rabbits document.
16. General examination will occur 4 times per day until wound is healed as indicated by slit lamp biomicroscopy (up to 7 days), then followed by once a day for the 7 days post wound closure followed by once every weekday until euthanasia.

Results

Summary of Each Rabbit
Surgery day 1, 20 Aug. 2018
Rabbit 1—ID #: 233665 Arrived 11 Jul. 2018 (Group 1-1 of 2).
Debridement procedure with 30% ethanol
Tx.—bioink
Outcome—Moderate conjunctival inflammation, wound healed just post 48 hours.
Rabbit 2—ID #: 233666 Arrived 11 Jul. 2018 (Group 1-2 of 2).
Debridement procedure with alcohol
Tx.—control (antibiotic drops only)
Outcome—Severe conjunctival inflammation and chemosis, lesion doubled in size, pain was initially difficult to control but much improved on the second day. Wound healed just post 48 hours.
Surgery day 2, 3 Sep. 2018
Rabbit 3—ID #: 239686 Arrived 1 Aug. 2018 (Group 2-1 of 5).
Perforation Procedure
Tx.—bioink
Outcome—Moderate conjunctival inflammation and secondary ulcer formation, perforation healed at 32 hours and secondary ulcer healed at 52 hours.
Rabbit 4—ID #: 239685 Arrived 1 Aug. 2018 (Group 2-2 of 5).
Perforation Procedure
Tx.—bioink Outcome—Moderate conjunctival inflammation and secondary ulcer formation, perforation healed at 28 hours and secondary ulcer healed at 48 hours.

Rabbit 5—ID #: 239684 Arrived 1 Aug. 2018 (Group 2-3 of 5).

Perforation Procedure

Tx.—control (cyanoacrylate glue)

Outcome—Moderate conjunctival inflammation and chemosis. Rabbit was quite uncomfortable and is less uncomfortable now with adequate pain management strategies being employed. Secondary ulcer formation was observed at 56 hours but that has now healed at 72 hours. Perforation wound healed at 80 hours.

Surgery day 3, 4 Sep. 2018—Reduction in povidone iodine concentration to 0.2% from 5% and addition of lubricating eye drops implemented Rabbit 6—ID #: 239687 Arrived 1 Aug. 2018 (Group 2-4 of 5).

Perforation Procedure

Tx.—bioink

Outcome—Healed at 8 hours, no complications. No additional analgesia from the first buprenorphine patch required.

Rabbit 7—ID #: 239688 Arrived 1 Aug. 2018 (Group 2-5 of 5).

Perforation Procedure

Tx.—control (cyanoacrylate glue)

Outcome—Rabbit was initially in significant pain with moderate conjunctivitis and significant chemosis that appeared to be in relation to the location of the cyanoacrylate glue. Euthanasia was considered, however she seemed to respond to the methadone administered and began eating that night. Upon examination this morning (day 2), the rabbit appeared to be more comfortable with her pain successfully managed—she is still uncomfortable but not suffering. The wound has healed at 48 hours and she is now comfortable.

In the epithelial defect wound model (rabbits 1 and 2), the control and treatment rabbits achieved wound healing at the same time point (FIG. 20). The treatment rabbit was administered significantly less post-operative analgesia and had overall pain scores that were less than what was experienced by the control rabbit (FIGS. 21 and 22). Pain scores were based on assessment of indicators including excessive blinking, blepharospasm, rubbing of the eye, blepharospasm, and lacrimation and rubbing of the eye.

In the corneal perforation model (rabbits 3, 4 and 5), wound healing occurred significantly faster in the treatment rabbits (t=28 and t=32 hours) as compared to the control rabbit (t=80 hours) (FIG. 23). Treatment rabbits also overall were administered less post-operative analgesia (FIGS. 25 and 26) as compared to the control rabbit (FIG. 24).

In the modified corneal perforation model (rabbits 6 and 7), wound healing occurred significantly faster in the treatment rabbit (t=8 hours) as compared to the control (t=48 hours) (FIG. 27). No post-operative analgesia was administered to the treatment rabbit and pain scores recorded were significantly less in the treatment rabbit as compared to the control (FIG. 28).

The bioink is biocompatible and does not hinder corneal wound healing. These results suggest that the bioink reduces pain associated with corneal injuries and may also accelerate wound healing in corneal perforations as compared to conventional treatment options.

Example Ten: Lyophilization and Reconstitution of the Bioink

Methods 50 uL of bioink components A and B were prepared.

Component A included 20% hPL, 4 mg/mL fibrinogen in DMEM/F12, and component B included 10 U/mL thrombin in DMEM/F12. Both components had final volume of 50 uL. Once mixed, they provided the same formulation as bioink 5 (Table 3, premixing concentration: 20% hPL, 4 mg/mL fibrinogen, 10 U/mL thrombin, DEME/F12).

Samples were freeze dried at −40 degree (FIG. 29A)

Reconstituted with 50 uL water each tube within seconds (FIG. 29B)

Mixed and adhesive and transparent gel formed (FIG. 29C)

Results

Visual assessment indicated that the bioink can still solidify within 2 minutes after re-constitution. It was observed to be adhesive (attached to the tip in FIG. 29C) and transparent. (FIG. 29C).

The invention claimed is:

1. A composition comprising 0.1-20 mg/ml fibrinogen, 2-20 U/mL thrombin, and 1-40% (v/v) platelet lysate.

2. The composition of claim 1, further comprising any one or more of: ions, an ion source, amino acids, fibronectin, anaesthetics, antibiotics, growth factors, tissue factor XIII, matrix proteins.

3. The composition of claim 2, wherein:
   (i) the ions comprise calcium ions, and/or the growth factors comprise human epidermal growth factor (hEGF); or
   (ii) the composition comprises a culture medium comprising the ions and amino acids; or
   (iii) the ions are components of an ionic salt solution included in the composition.

4. The composition of claim 1, wherein:
   (i) the composition further comprises cells, mammalian cells, or human cells; or
   (ii) the platelet lysate comprises or consists of human platelet lysate.

5. The composition of claim 1, wherein the composition comprises:
   (i) 0.1-15 mg/ml fibrinogen; 2-15 U/ml thrombin; and 5-40% (v/v) platelet lysate; or
   (ii) less than 1 mg/ml fibrinogen; 2-20 U/ml thrombin; and 5-40% (v/v) platelet lysate.

* * * * *